United States Patent
Petryk et al.

(10) Patent No.: US 7,943,813 B2
(45) Date of Patent: May 17, 2011

(54) ABSORBENT PRODUCTS WITH ENHANCED REWET, INTAKE, AND STAIN MASKING PERFORMANCE

(75) Inventors: Teresa De Jesus Petryk, Woodstock, GA (US); Jason Matthew English, Menasha, WI (US); Rebecca Willey Griffin, Woodstock, GA (US); Varunesh Sharma, Atlanta, GA (US); Patricia A. Stern, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1458 days.

(21) Appl. No.: 10/331,823

(22) Filed: Dec. 30, 2002

(65) Prior Publication Data

US 2004/0127872 A1 Jul. 1, 2004

(51) Int. Cl.
*A61F 13/15* (2006.01)
(52) U.S. Cl. ........ 604/367; 604/359; 604/360; 604/364; 604/365; 604/366; 604/381
(58) Field of Classification Search .................. 604/367, 604/359, 360, 364, 365, 366, 381, 382
See application file for complete search history.

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,692,618 A | 9/1972 | Dorschner et al. |
| 3,802,817 A | 4/1974 | Matsuki et al. |
| RE28,219 E | 10/1974 | Taylor et al. |
| 3,849,241 A | 11/1974 | Butin et al. |
| 3,855,046 A | 12/1974 | Hansen et al. |
| 4,100,324 A | 7/1978 | Anderson et al. |
| 4,124,673 A | 11/1978 | Pieper et al. |
| 4,303,924 A | 12/1981 | Young, Jr. |
| 4,340,563 A | 7/1982 | Appel et al. |
| 4,375,448 A | 3/1983 | Appel et al. |
| 4,382,262 A | 5/1983 | Savit |

(Continued)

FOREIGN PATENT DOCUMENTS

DE 2313335 1/1975

(Continued)

OTHER PUBLICATIONS

RD 173017, filed Sep. 10, 1978, (abstract).

(Continued)

*Primary Examiner* — Jacqueline F Stephens
(74) *Attorney, Agent, or Firm* — Steven D. Flack; Richard M. Shane; Bryan R. Rosiejka

(57) ABSTRACT

An absorbent article, such as a feminine care product, includes a liquid permeable liner layer, a generally liquid impermeable outer cover layer, and an absorbent layer disposed between the liner layer and outer cover layer. Spaced apart solidified deposits of a phase-change liquid are defined on either the liner layer top surface, bottom surface or both surfaces, and/or other layers along the other layers' upper or lower surfaces. The deposits are defined such that areas of the liner layer top surface are exposed thereby being permeable to bodily exudates insulting the article between the deposits while acting as a barrier against liquid that may flow back to the liner layer or other treated layers from the absorbent layer or other layers contained in the absorbent article.

24 Claims, 6 Drawing Sheets

U.S. PATENT DOCUMENTS

| | | |
|---|---|---|
| 4,389,503 A | 6/1983 | Maxwell et al. |
| 4,478,910 A | 10/1984 | Oshima et al. |
| 4,494,278 A | 1/1985 | Kroyer et al. |
| 4,503,444 A | 3/1985 | Tacklind |
| 4,504,357 A | 3/1985 | Holbein et al. |
| 4,623,340 A | 11/1986 | Luceri |
| 4,640,810 A | 2/1987 | Laursen et al. |
| 4,684,956 A | 8/1987 | Ball |
| 4,689,078 A | 8/1987 | Koike et al. |
| 4,758,276 A | 7/1988 | Lin et al. |
| 4,762,520 A | 8/1988 | Wallstrom |
| 4,778,458 A | 10/1988 | Gronostajski |
| 4,786,288 A | 11/1988 | Handa et al. |
| 4,795,668 A | 1/1989 | Krueger et al. |
| 4,841,310 A | 6/1989 | Hoffman |
| 4,849,770 A | 7/1989 | Koike et al. |
| 4,909,879 A | 3/1990 | Ball |
| 4,940,464 A | 7/1990 | Van Gompel et al. |
| 4,969,951 A | 11/1990 | Koike et al. |
| 5,057,368 A | 10/1991 | Largman et al. |
| 5,069,970 A | 12/1991 | Largman et al. |
| 5,087,283 A | 2/1992 | Dixon et al. |
| 5,108,820 A | 4/1992 | Kaneko et al. |
| 5,195,950 A | 3/1993 | Delannoy |
| 5,214,442 A | 5/1993 | Roller |
| 5,277,976 A | 1/1994 | Hogle et al. |
| 5,280,310 A | 1/1994 | Otsuka et al. |
| 5,284,703 A | 2/1994 | Everhart et al. |
| 5,336,552 A | 8/1994 | Strack et al. |
| 5,350,624 A | 9/1994 | Georger et al. |
| 5,371,520 A | 12/1994 | Kubota |
| 5,382,400 A | 1/1995 | Pike et al. |
| 5,431,643 A * | 7/1995 | Ouellette et al. ......... 604/385.05 |
| 5,454,801 A | 10/1995 | Lauritzen |
| 5,458,590 A | 10/1995 | Schleinz et al. |
| 5,466,410 A | 11/1995 | Hills |
| 5,481,281 A | 1/1996 | Otsuka et al. |
| 5,486,166 A | 1/1996 | Bishop et al. |
| 5,490,846 A | 2/1996 | Ellis et al. |
| 5,503,076 A | 4/1996 | Yeo |
| 5,527,171 A | 6/1996 | Soerensen |
| 5,533,991 A | 7/1996 | Kirby et al. |
| 5,540,992 A | 7/1996 | Marcher et al. |
| 5,562,037 A | 10/1996 | Schleinz et al. |
| 5,563,642 A | 10/1996 | Keefe et al. |
| 5,565,022 A | 10/1996 | Wickramanayake |
| 5,566,616 A | 10/1996 | Schleinz et al. |
| 5,571,586 A | 11/1996 | Gobran |
| 5,591,153 A | 1/1997 | Mattingly, III |
| 5,597,642 A | 1/1997 | Schleinz et al. |
| 5,613,962 A | 3/1997 | Kenmochi et al. |
| 5,620,742 A | 4/1997 | Lauritzen |
| 5,629,063 A | 5/1997 | Gobran |
| 5,648,805 A | 7/1997 | Keefe et al. |
| 5,670,004 A | 9/1997 | Mattingly, III |
| 5,681,645 A | 10/1997 | Strack et al. |
| 5,694,739 A | 12/1997 | Mattingly, III |
| 5,695,855 A | 12/1997 | Yeo et al. |
| 5,759,673 A | 6/1998 | Ikezawa et al. |
| 5,769,837 A | 6/1998 | Parr |
| 5,820,973 A | 10/1998 | Dodge, II et al. |
| 5,834,114 A | 11/1998 | Economy et al. |
| 5,851,274 A | 12/1998 | Lin |
| 5,853,859 A | 12/1998 | Levy et al. |
| 5,883,231 A | 3/1999 | Achter et al. |
| 5,895,505 A | 4/1999 | Yamamoto et al. |
| 5,931,824 A | 8/1999 | Stewart et al. |
| 5,938,826 A | 8/1999 | Baker et al. |
| 5,972,082 A | 10/1999 | Koyano et al. |
| 5,985,396 A | 11/1999 | Kerins et al. |
| 6,013,347 A | 1/2000 | Martin et al. |
| 6,024,220 A | 2/2000 | Smith et al. |
| 6,050,666 A | 4/2000 | Yeoh et al. |
| 6,051,036 A | 4/2000 | Kusaki et al. |
| 6,096,412 A | 8/2000 | McFarland et al. |
| 6,103,364 A | 8/2000 | Harris et al. |
| 6,106,922 A | 8/2000 | Cejka et al. |
| 6,120,783 A | 9/2000 | Roe et al. |
| 6,120,888 A | 9/2000 | Dolsey et al. |
| 6,132,858 A | 10/2000 | Kloos |
| 6,140,551 A | 10/2000 | Niemeyer et al. |
| 6,141,799 A | 11/2000 | Morris |
| 6,146,770 A | 11/2000 | Sargeant et al. |
| 6,149,259 A | 11/2000 | Otsuka et al. |
| 6,149,934 A | 11/2000 | Krzysik et al. |
| 6,150,005 A | 11/2000 | Williams et al. |
| 6,159,581 A | 12/2000 | Yoneda et al. |
| 6,199,968 B1 | 3/2001 | Katakura et al. |
| 6,231,652 B1 | 5/2001 | Koyano et al. |
| 6,235,098 B1 | 5/2001 | Maekawa et al. |
| 6,245,410 B1 | 6/2001 | Hahnle et al. |
| 6,254,582 B1 | 7/2001 | O'Donnell et al. |
| 6,258,427 B1 | 7/2001 | Kerins et al. |
| 6,258,997 B1 | 7/2001 | Johansson et al. |
| 6,263,816 B1 | 7/2001 | Codos et al. |
| 6,265,053 B1 | 7/2001 | Kronzer et al. |
| 6,266,436 B1 | 7/2001 | Bett et al. |
| 2001/0024716 A1 | 9/2001 | Chen et al. |
| 2002/0068917 A1 | 6/2002 | VanGompel et al. |
| 2002/0077618 A1 | 6/2002 | Molas |
| 2002/0128615 A1 | 9/2002 | Tyrrell et al. |

FOREIGN PATENT DOCUMENTS

| | | |
|---|---|---|
| DE | 2340855 | 6/1975 |
| DE | 25 13 251 | 9/1976 |
| DE | 2654823 | 6/1978 |
| DE | 2412852 | 5/1979 |
| DE | 19803827 | 8/1999 |
| DE | 19810847 | 9/1999 |
| DE | 19810849 | 5/2000 |
| EP | 0 023 433 | 2/1981 |
| EP | 0 211 524 | 2/1987 |
| EP | 0 140 560 | 11/1988 |
| EP | 0 392 528 | 10/1990 |
| EP | 0 471 384 | 2/1992 |
| EP | 0 526 225 | 2/1993 |
| EP | 0 604 729 | 7/1994 |
| EP | 0 639 459 | 2/1995 |
| EP | 0 713 774 | 5/1996 |
| EP | 0 748 894 | 12/1996 |
| EP | 0 764 550 | 3/1997 |
| EP | 0 805 027 | 11/1997 |
| EP | 0 809 680 | 12/1998 |
| EP | 0 698 138 | 7/1999 |
| EP | 0 951 889 | 10/1999 |
| EP | 1 059 340 | 12/2000 |
| EP | 1 070 596 | 1/2001 |
| EP | 0 777 008 | 4/2001 |
| EP | 1 099 434 | 5/2001 |
| EP | 0 746 296 | 6/2001 |
| EP | 1 120 097 | 8/2001 |
| EP | 1 164 007 | 12/2001 |
| EP | 1 166 732 | 1/2002 |
| EP | 1 186 431 | 3/2002 |
| EP | 0 861 154 | 4/2002 |
| EP | 1 062 095 | 6/2002 |
| FR | 2741296 | 5/1997 |
| GB | 807768 | 1/1959 |
| GB | 2 128 439 | 4/1984 |
| GB | 2 334 684 | 9/1999 |
| JP | 55-051 583 A2 | 4/1980 |
| JP | 57-115 352 A2 | 7/1982 |
| JP | 60-104 076 A2 | 6/1985 |
| JP | 85-027 588 B | 6/1985 |
| JP | 60-169 489 A2 | 9/1985 |
| JP | 60-245 557 A2 | 12/1985 |
| JP | 61-118 473 A2 | 6/1986 |
| JP | 61-179 269 A2 | 8/1986 |
| JP | 61-179 271 A2 | 8/1986 |
| JP | 61-179 272 A2 | 8/1986 |
| JP | 61-179 273 A2 | 8/1986 |
| JP | 63-265 680 A2 | 11/1988 |
| JP | 01-013 518 A2 | 1/1989 |
| JP | 03-104 646 A2 | 5/1991 |
| JP | 03-049 311 B4 | 7/1991 |
| JP | 92-015 746 B | 3/1992 |
| JP | 04-251747 A | 9/1992 |

| | | |
|---|---|---|
| JP | 04-292 947 A2 | 10/1992 |
| JP | 05-035 191 B4 | 5/1993 |
| JP | 05-230 409 A2 | 9/1993 |
| JP | 05-247 390 A2 | 9/1993 |
| JP | 05-331 396 A2 | 12/1993 |
| JP | 06-127 032 A2 | 5/1994 |
| JP | 06-246 934 A2 | 9/1994 |
| JP | 06-286 134 A2 | 10/1994 |
| JP | 06-312 509 A2 | 11/1994 |
| JP | 07-034 019 A2 | 2/1995 |
| JP | 07-068 922 A2 | 3/1995 |
| JP | 07-089 077 A2 | 4/1995 |
| JP | 07-125 197 A2 | 5/1995 |
| JP | 07-156 407 A2 | 6/1995 |
| JP | 07-213 310 A | 8/1995 |
| JP | 07-241 983 A2 | 9/1995 |
| JP | 07-304 167 A2 | 11/1995 |
| JP | 07-314 694 A2 | 12/1995 |
| JP | 07-314 728 A2 | 12/1995 |
| JP | 07-323 657 A2 | 12/1995 |
| JP | 08-052 903 A2 | 2/1996 |
| JP | 08-118 617 A2 | 5/1996 |
| JP | 08-164 602 A2 | 6/1996 |
| JP | 08-174 995 A2 | 7/1996 |
| JP | 08-187 933 A2 | 7/1996 |
| JP | 08-216 395 A2 | 8/1996 |
| JP | 08-259 868 A2 | 10/1996 |
| JP | 08-267 733 A2 | 10/1996 |
| JP | 08-309 987 A2 | 11/1996 |
| JP | 09-031 866 A2 | 2/1997 |
| JP | 09-039 233 A2 | 2/1997 |
| JP | 2 593 830 B2 | 3/1997 |
| JP | 09-057 966 A2 | 3/1997 |
| JP | 09-066 661 A2 | 3/1997 |
| JP | 2 618 359 B2 | 6/1997 |
| JP | 09-175 004 A2 | 7/1997 |
| JP | 09-175 005 A2 | 7/1997 |
| JP | 09-175 006 A2 | 7/1997 |
| JP | 09-175 007 A2 | 7/1997 |
| JP | 09-194 781 A2 | 7/1997 |
| JP | 09-226 229 A2 | 9/1997 |
| JP | 09-240 138 A2 | 9/1997 |
| JP | 09-268 482 A2 | 10/1997 |
| JP | 09-268 484 A | 10/1997 |
| JP | 09-286 102 A2 | 11/1997 |
| JP | 09-314 984 A2 | 12/1997 |
| JP | 10-034 967 A2 | 2/1998 |
| JP | 10-044 408 A2 | 2/1998 |
| JP | 2 732 999 B2 | 3/1998 |
| JP | 2 758 788 B2 | 5/1998 |
| JP | 10-138 504 A2 | 5/1998 |
| JP | 10-138 510 A2 | 5/1998 |
| JP | 10-138 516 A2 | 5/1998 |
| JP | 10-138 520 A2 | 5/1998 |
| JP | 10-138 521 A2 | 5/1998 |
| JP | 10-193 610 A2 | 7/1998 |
| JP | 10-264 498 A2 | 10/1998 |
| JP | 10-278 312 A2 | 10/1998 |
| JP | 11-010 852 A2 | 1/1999 |
| JP | 11-010 853 A2 | 1/1999 |
| JP | 11-061 021 A2 | 3/1999 |
| JP | 11-099 646 A2 | 4/1999 |
| JP | 11-188 968 A2 | 7/1999 |
| JP | 11-207 951 A2 | 8/1999 |
| JP | 11-268 284 A2 | 10/1999 |
| JP | 11-268 405 A2 | 10/1999 |
| JP | 11-277 772 A2 | 10/1999 |
| JP | 2000-000 266 A | 1/2000 |
| JP | 2000-043 401 A2 | 2/2000 |
| JP | 2000-052 640 A2 | 2/2000 |
| JP | 2000-127 611 A2 | 5/2000 |
| JP | 2000-190 628 A2 | 7/2000 |
| JP | 2000-203 150 A2 | 7/2000 |
| JP | 2000-233 571 A2 | 8/2000 |
| JP | 3 089 308 B2 | 9/2000 |
| JP | 3 089 583 B2 | 9/2000 |
| JP | 2000-238 410 A2 | 9/2000 |
| JP | 2000-256 974 A2 | 9/2000 |
| JP | 2000-296 670 A | 10/2000 |
| JP | 2001-010 031 A2 | 1/2001 |
| JP | 2001 018 518 A2 | 1/2001 |
| JP | 2001 020 185 A2 | 1/2001 |
| JP | 2001 039 017 A2 | 2/2001 |
| NL | 9400024 A | 8/1995 |
| WO | WO 97/18090 | 5/1997 |
| WO | WO 98/36722 | 8/1998 |
| WO | WO 98/43821 | 10/1998 |
| WO | WO 99/33669 | 7/1999 |
| WO | WO 99/43760 | 9/1999 |
| WO | WO 99/65700 | 12/1999 |
| WO | WO 00/07426 | 2/2000 |
| WO | WO 00/07821 | 2/2000 |
| WO | WO 00/35401 | 6/2000 |
| WO | WO 00/37009 | 6/2000 |
| WO | WO 00/40195 | 7/2000 |
| WO | WO 00/40196 | 7/2000 |
| WO | WO 00/42960 | 7/2000 |
| WO | WO 00/56972 | 9/2000 |
| WO | WO 00/69950 | 11/2000 |
| WO | WO 00/72984 | 12/2000 |
| WO | WO 00/73063 | 12/2000 |
| WO | WO 01/02254 | 1/2001 |
| WO | WO 01/31122 | 5/2001 |
| WO | WO 01/31124 | 5/2001 |
| WO | WO 01/32318 | 5/2001 |
| WO | WO 01/36171 | 5/2001 |
| WO | WO 01/36209 | 5/2001 |
| WO | WO 01/45757 | 6/2001 |
| WO | WO 01/49230 | 7/2001 |
| WO | WO 01/50412 | 7/2001 |
| WO | WO 01/97972 | 12/2001 |
| WO | WO 02/14080 | 2/2002 |
| WO | 03/013406 | 2/2003 |
| WO | 03/043554 | 5/2003 |

OTHER PUBLICATIONS

Pages 198-201 of Ink Jet Technology and Product Development Strategies, by Stephen F. Pond, copyright 2000, of Torrey Pines Research.

Material Safety Data Sheet; Hot Melt Ink, Cyan, Magenta, Yellow, etc.; pp. 1-3.

Material Safety Data Sheet; Hot Melt Ink, Black, High; JET 7520/ JET 7533; pp. 1-4.

Sales Literature; Oct. 1, 2002; Spectra Inc.; "Galaxy PH 256/80 HM".

* cited by examiner

ABSORBENT PRODUCTS WITH ENHANCED REWET, INTAKE, AND STAIN MASKING PERFORMANCE

FIELD OF THE INVENTION

The invention pertains to absorbent articles, and in particular, feminine care products such as feminine care pads/sanitary napkins and pantiliners. More specifically, the invention pertains to methods for modifying liquid handling performance of such absorbent article-type products.

BACKGROUND OF THE INVENTION

Consumer personal care product manufacturers are routinely looking for ways to improve the performance attributes of disposable absorbent articles, and in particular feminine care products such as feminine care sanitary napkins and pads. Absorbent articles including feminine care products, are typically manufactured such that they include at least three discernable components. These components are frequently incorporated into a laminate-type structure. The first of these components is a body-side or skin contacting liner layer. The body-side liner layer (or cover sheet layer) is in contact with the skin during product use, and functions as a liquid permeable passage layer, through which excreted body exudates travel. Such liner layer also functions in some circumstances to mask any staining that may occur in a feminine care product, as body fluid passes through it to settle in a second or more remote layer. In this regard, it has been found that a segment of consumers prefer not to view feminine product staining during product use.

Such liner layers may often be made of nonwoven materials, and may, in some instances, be chemically treated to impart desired attributes. For instance, the liner layer surface may be treated so that it demonstrates hydrophilicity.

At least one absorbent layer (or liquid retention layer) is typically positioned under the liner layer and in liquid communication (liquid can travel from one layer to the other, either directly or indirectly) with such liner. The absorbent layer(s) may also be made of a nonwoven material, and may further include materials with known or enhanced absorbency attributes, such as superabsorbents and cellulosic-based materials. The absorbent layer may also be made from nonwoven materials that have been chemically treated to impart desired properties, such as hydrophilicity. For example, the absorbent layer may be treated with surfactants to make it more wettable since the layer essentially functions to retain the excreted liquids within the feminine care product. Finally, the absorbent layer may be made from a variety of nonwoven fibers, to impart a variety of attributes to the product.

A third layer (or additional layer if more than one absorbent layer is used) is typically positioned under the absorbent layer(s), on a side opposite to that of the body-side liner layer. This third layer, known as the baffle or backsheet, functions to both retain the absorbed exudates within the absorbent article, for instance the feminine product, and also to protect the clothing/garments of a consumer wearing such product, from becoming soiled. This backsheet is frequently made from a liquid impervious hydrophobic material such as a film material, or other liquid impervious nonwoven material. The liner layer and the backsheet may each extend laterally beyond the absorbent layer and be bonded together to form a peripheral seal around the article. The feminine care products are positioned in use in the crotch portion of an undergarment for absorption of body exudates, while other absorbent articles are positioned around the crotch/and waist areas while in use.

It should be recognized that manufacturers of such absorbent articles may utilize additional layers so as to impart improved performance to such products, such as fluid transfer layers or surge layers, that can aid in capturing relatively large and sudden onsets of body exudates (discharges), before passing the exudates to the absorbent layer. Such layers may additionally be used to temporarily hold and distribute absorbed liquids (distribution layers or fluid transfer/delay layers) to more distant positions in the absorbent layer of the pad, whereby the pad more efficiently captures moisture within the absorbent layer, rather than in discrete narrow areas immediately under or adjacent to the target area or original discharge location.

Further, an adhesive layer may be employed in the case of certain feminine care products, on a portion of, or the entire backsheet layer on a side which would face a user's garments during use (opposite to that of the absorbent layer), so as to improve the ability of the product to remain fixed or motionless while in use (i.e. to prevent slippage of the product while in use). If an adhesive layer is employed, it is typically used concurrently with a removable and protective adhesive cover sheet or release paper, that is removed by the consumer prior to use. Such cover sheet may be made from a film material or a coated paper for example, and is positioned such that it covers the adhesive on the backsheet.

Manufacturers of such absorbent articles, and in particular, feminine care products, have regularly sought to improve the liquid handling performance, such as the liquid intake properties of such products so as to reduce risks of leakage during use. Further, such manufacturers have previously identified the desire among consumers to reduce the "rewet", associated with such products. That is, manufacturers have sought to reduce the sensation of moisture returning to the skin-contacting surface, from the absorbent layer(s) of such products during use. Moisture on the skin may lead to discomfort.

Additionally, it has been found that while some women who use such products are interested in being able to receive a visual cue as to when such products are used or soiled, there is a desire in other women from an aesthetic point or view, to reduce the level of staining which can be seen after a product has been used, or while a product is being used. To these ends, there continue to be needs in the personal care area for feminine care products which demonstrate increased abilities to remove excreted fluids and that do such without the perception of staining. There is further a need to reduce the perceived rewet of such a product during use. It is to such needs that the current invention is directed.

Drop on demand, valve jet and continuous ink jet printing apparatus have been used to apply inks to a variety of substrates for a period of time. Generally, a drop on demand ink jet printing apparatus operates to discharge individual droplets of ink onto a substrate in a predetermined pattern to be printed. Continuous ink jet printing apparatus are ink jet printing apparatus which produce a continuous flow of ink jet ink onto a substrate. Ink jet printing is a non-impact and non-contact printing method in which an electronic signal controls and directs the droplets or stream of ink that can be deposited on a wide variety of substrates. Current drop on demand ink jet printing technology involves forcing the ink drops through small nozzles by piezoelectric pressure, thermal ejection, or oscillation, and onto the surface of a material/media. Ink jet printing is extremely versatile in terms of the variety of substrates that can be treated, as well as the print quality and the speed of operation that can be achieved. In addition, ink jet printing is digitally controllable. For these reasons, ink jet printing methodology has been widely adopted for industrial marking and labeling. In addition, ink jet printing methodology has also found widespread use in architectural and engineering design applications, medical imaging, office printing (of both text and graphics), geographical imaging systems (e.g., for seismic data analysis and mapping), signage, in display graphics (e.g., photographic reproduction, business and courtroom graphics, graphic arts), and the like. Finally, ink jet printing has now also been used to create an image on a variety of textile and nonwoven substrates. While such ink jet printers have been used to print on discrete areas, usually for ornamental or aesthetic reasons, there is a need for use of such efficient technology to provide enhanced rewet and stain masking protection to feminine care and other personal care products. It is to such needs that the present invention is also directed.

SUMMARY OF THE INVENTION

An absorbent article having at least a liner layer, an absorbent layer and a backsheet layer includes solidified deposits across at least one surface of one of the layers contained in the absorbent article and desirably such that less than or equal to 80% of the at least one surface is covered across the surface. In an alternative embodiment less than or equal to 75% of the at least one surface is covered across the surface. In a further alternative embodiment, the target area is covered across, and alternatively printed across, that is the middle 75% surface area (in the width dimension) of the treated article layer is covered across (either liner or surge layer surfaces, or both).

Desirably, an absorbent article includes a liquid permeable liner layer having a top surface and a lower surface. The surfaces define a liner surface area. The absorbent article also includes a generally liquid impermeable outer cover and an absorbent layer disposed between the liner layer lower surface and the outer cover. The absorbent article further includes a series of spaced apart solidified deposits of a liquid impermeable material defined on a liner layer surface. Less than or equal to 80% of the liner surface area is covered with the spaced apart solidified deposits. Desirably less than or equal to 75% is covered in an alternative embodiment. In one embodiment, the solidified deposits are located on the liner top surface. In an alternative embodiment, the solidified deposits are located on the liner lower surface. In still another alternative embodiment, the solidified deposits are located throughout the thickness of the liner layer, such that they are on both the top and lower surfaces. In still another alternative embodiment, the solidified deposits are located on at least one of the liner surfaces.

In one embodiment the absorbent article has deposits that include spaced apart continuous stripes disposed on at least one of the liner surfaces. In a further embodiment the absorbent article deposits are a phase change liquid. In still another embodiment, the phase change liquid is a hot melt wax that has been printed on the absorbent article.

In still another embodiment of the invention, a feminine care product includes a liquid permeable liner layer having a top surface and a lower surface; a generally liquid impermeable outer cover layer; an absorbent layer disposed between the liner layer lower surface and the outer cover layer; spaced apart solidified deposits of a phase-change liquid defined on the liner layer top surface across the top surface of the liner layer.

In still another embodiment the solidified deposits are in the pattern of an aesthetically pleasing design. Yet in another embodiment of the invention a feminine care product includes an absorbent layer containing superabsorbent material homogeneously distributed, from between about 5-50% by weight of the absorbent layer. In still a further alternative embodiment, the superabsorbent material is homogeneously distributed between about 10-30% by weight of the absorbent layer.

Still in a further alternative embodiment of the invention, the absorbent article includes a surge layer having a top and lower surface that is positioned between the liner layer and the absorbent layer, with the top surface facing the liner layer lower surface. In still a further alternative embodiment, at least one surface of the surge layer includes solidified deposits.

A method of creating a feminine care product with reduced rewet properties includes the steps of depositing substances capable of solidifying upon a feminine care product substrate, wherein at least one image is formed on the substrate in discrete areas across the substrate surface, such that 80% or less surface area across the substrate is covered with the image. In an alternative method 75% or less surface area across the substrate is covered with the image. In a further alternative method, the target area is covered, alternatively, printed across, that is the middle 75% surface area of the product (either liner or surge layer surfaces, or both).

A method of creating a feminine care product with reduced rewet properties includes the steps of providing a print head capable of processing phase change inks, providing a phase change ink, providing a feminine care product substrate, activating the printhead such that the ink passes therethrough, and passing the substrate under the printhead, wherein at least one image is formed on the substrate in discrete areas across the substrate surface, such that 75% or less surface area across the substrate is covered with a printed image.

DETAILED DESCRIPTION

Definitions

Figure 1:
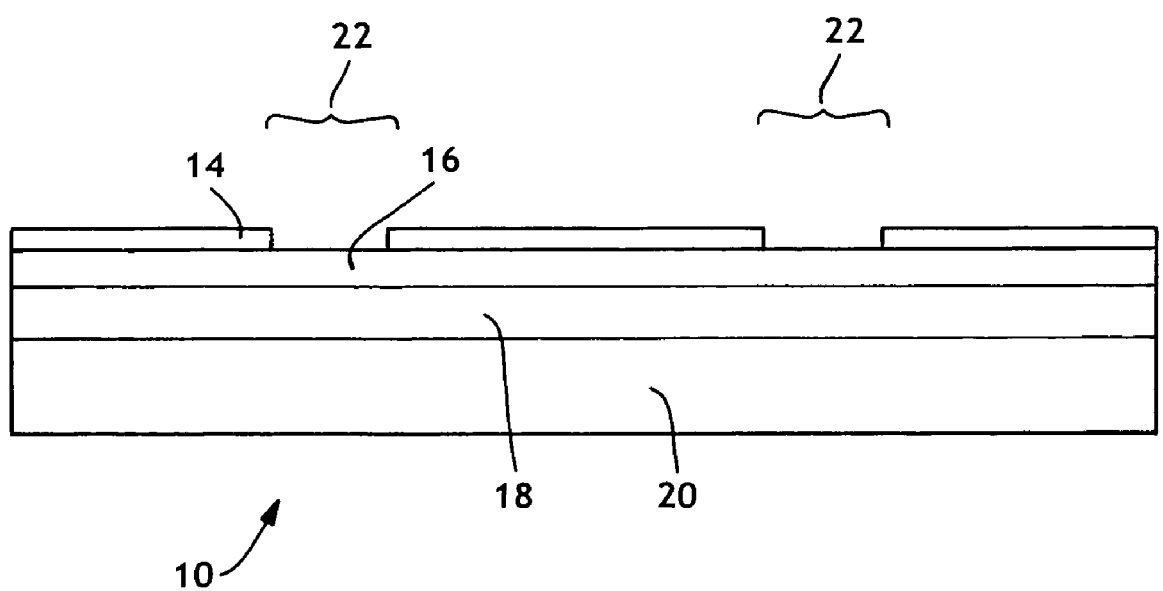
FIG. 1 illustrates a cross sectional view of a feminine care product (pad) in accordance with the invention.

For the purposes of this application the term "simulant", shall be used synonymously with "menses simulant" and "artificial menses", and shall mean a material that is described as follows, that has been designed to mimic the physical attributes and characteristics of a feminine discharge.

The artificial menses fluid used in the testing was made according to U.S. Pat. No. 5,883,231 from blood and egg white by separating the blood into plasma and red cells and separating the white into thick and thin portions, where "thick" means it has a viscosity after homogenization above about 20 centipoise at 150 sec$^{-1}$, combining the thick egg white with the plasma and thoroughly mixing, and finally adding the red cells and again thoroughly mixing. A more detailed procedure for formulation follows:

Blood, in this example defibrinated swine blood, is separated by centrifuging at 3000 rpm for 30 minutes, though other methods or speeds and times may be used if effective. The plasma is separated and stored separately, the buffy coat removed and discarded and the packed red blood cells stored separately as well. It should be noted that the blood must be treated in some manner so that it may be processed without coagulating. Various methods are known to those skilled in the art, such as defibrinating the blood to remove the clotting fibrous materials, the addition of anti-coagulant chemicals and others. The blood must be non-coagulating in order to be useful and any method which accomplishes this without damaging the plasma and red cells is acceptable.

Jumbo chicken eggs are separated, the yolk and chalazae discarded and the egg white retained. The egg white is separated into thick and thin portions by straining the white through a 1000 micron nylon mesh for about 3 minutes, and the thinner portion discarded. The thick portion of egg white, which is retained on the mesh, is collected and drawn into a 60 cc syringe, which is then placed on a programmable syringe pump and homogenized by expelling and refilling the contents five times. The amount of homogenization is controlled by the syringe pump rate of about 100 ml/min, and the tubing inside diameter of about 0.12 inches. After homogenizing, the thick egg white has a viscosity of about 20 centipoise at 150 $sec^{-1}$ and is then placed in the centrifuge and spun to remove debris and air bubbles at about 3000 rpm for about 10 minutes After centrifuging, the thick, homogenized egg white, which contains ovamucin, is added to a 300 cc FENWAL Transfer pack container using a syringe. Then 60 cc of the swine plasma is added to the FENWAL Transfer pack container. The FENWAL Transfer pack container is clamped, all air bubbles removed, and placed in a Stomacher lab blender where it is blended at normal (or medium) speed for about 2 minutes. The FENWAL transfer pack container is then removed from the blender, 60 cc of swine red blood cells are added, and the contents mixed by hand kneading for about 2 minutes or until the contents appear homogenous. A hematocrit of the final mixture should show a red blood cell content of about 30 weight percent and generally should be at least within a range of 28-32 weight percent for artificial menses made according to this example. The amount of egg white is about 40 weight percent.

The ingredients and equipment used in the preparation of artificial menses are readily available. Below is a listing of sources for the items used, though of course other sources may be used providing they are approximately equivalent.

Blood (swine): Cocalico Biologicals, Inc., 449 Stevens Rd., Reamstown, Pa. 17567, (717) 336-1990.

Fenwal Transfer pack container, 300 ml, with coupler, code 4R2014: Baxter Healthcare Corporation, Fenwal Division, Deerfield, Ill. 60015.

Harvard Apparatus Programmable Syringe Pump model no. 55-4143: Harvard Apparatus, South Natick, Mass. 01760.

Stomacher 400 laboratory blender model no. BA 7021, serial no. 31968: Seward Medical, London, England, UK.

1000 micron mesh, item no. CMN-1000-B: Small Parts, Inc., PO Box 4650, Miami Lakes, Fla. 33014-0650, 1-800-220-4242.

Hemata Stat-II device to measure hemocrits, serial no. 1194Z03127: Separation Technology, Inc., 1096 Rainer Drive, Altamont Springs, Fla. 32714.

The term "Intake" includes the initial absorption of fluid into a dry product as well as the continued uptake of that fluid into the absorbent structure of a wet or insulted product.

The term "rewet" shall refer to the property of moisture to pass through a first layer and be drawn or move back to the first layer through which it passed from a second layer that is in fluid communication with the first layer (either directly or indirectly). The term shall also mean for the purposes of this application, the sensation of moisture on a particular layer of laminate material, but for the most part, the liner layer. The rewet of a material shall be measured in grams by the following test methods as noted.

The single intake test or the triple intake test was performed as noted. These tests are used to determine the intake time of a known quantity of fluid into a material and/or a material system. The test apparatus consists of clear, preferably acrylic rate blocks as will be described.

Figure 3:
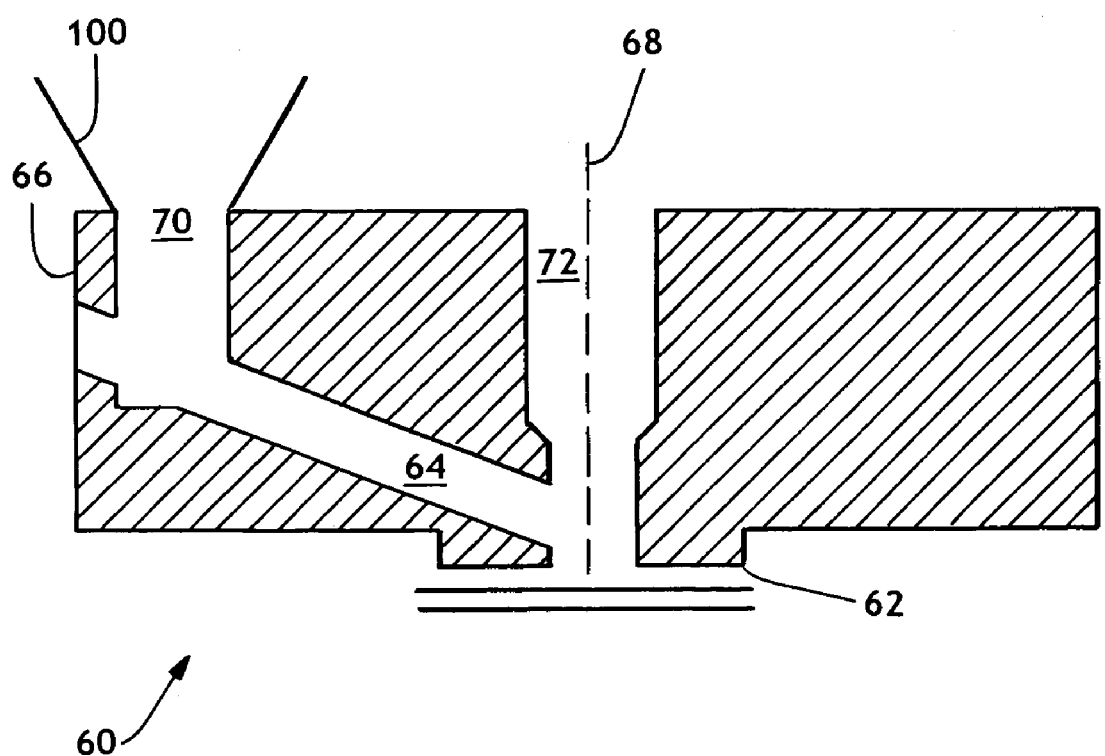
FIG. 3 is a cross-sectional diagram of a rate block apparatus suitable for use in determining fluid intake time of a material or material systems, such as to be used with a feminine care product of the present invention.

Equipment Needed:

Acrylic rate blocks as shown in FIG. 3. The test apparatus consists of a clear, preferably acrylic, rate block 60 as shown in FIG. 3, which is a cross-sectional diagram of a rate block apparatus suitable for use in determining fluid intake time of a material or material system. The rate block 60 is 3 inches (76.2 mm) wide and 2.87 inches (72.9 mm) deep (into the page) and has an overall height of 1.125 inches (28.6 mm) which includes a center area 62 on the bottom of the rate block 60 that projects farther from the main body of the rate block 60 and has a height of 0.125 inches (3.2 mm) and a width of 0.886 inches (22.5 mm). The rate block 60 has a capillary 64 with an inside diameter of 0.186 inches (4.7 mm) that extends diagonally downward from one side 66 to the center line 68 at an angle of 21.8 degrees from the horizontal. The capillary 64 may be made by drilling the appropriately sized hole from the side 66 of the rate block 60 at the proper angle beginning at a point 0.726 inches (18.4 mm) above the bottom of the rate block 60; provided, however, that the starting point of the drill hole in the side 66 must be subsequently plugged so that test fluid will not escape there. The top hole 70 has a diameter of 0.312 inches (7.9 mm), and a depth of 0.625 inches (15.9 mm) so that it intersects the capillary 64. The top hole 70 is perpendicular to the top of the rate block 60 and is centered 0.28 inches (7.1 mm) from the side 66. The top hole 70 is the aperture into which the funnel 100 is placed. The center hole 72 is for the purpose of viewing the progression of the test fluid and is actually of an oval shape into the plane of FIG. 3. The center hole 72 is centered width-wise on the rate block 60 and has a bottom hole width of 0.315 inches (8 mm) and length of 1.50 inches (38.1 mm) from center to center of 0.315 inch (8 mm) diameter semi-circles making up the ends of the oval. The oval enlarges in size above 0.44 inches (11.2 mm) from the bottom of the rate block 60, for ease of viewing, to a width of 0.395 inches (10 mm) and a length of 1.930 inches (49 mm). The top hole 70 and center hole 72 may also be made by drilling.

Other Equipment and Materials Needed Include:

P-5000 pipette with RC-5000 tips and foam pipette insert.

Small beaker

Menses simulant (made according to directions above) warmed in bath at about 23° C. for 30 minutes or more Small spatula (stirrer)

Bench liner 2 stopwatches 1-2 timers

Gauze squares for cleaning stimulant (Rewet portion of test)

Automatic Blood Strikethrough (AM 1995) Machine which consists of a bag of water on a stand that is driven by an air pump (Omega Engineering, Inc. Model HHP 701) which compresses the bag at 1 psi for 3 minutes. PIPETMAN Pipetter, Model P-5000 obtained from Rainin Instrument Company, Inc. of Woburn, Mass.

Blotter, James River Verigood brand, 100 LB, cut to 3" by 5"

Preparation for All Tests:

Allow a bag of menses simulant to equilibrate for 30 minutes in a water bath at 23 degrees C. Before opening, the bag is massaged and gently squeezed to mix the formulation, which may have separated during storage. Pour simulant into a beaker. Stir the simulant gently to swirl in the beaker frequently.

Cut all material components of the composite to be tested at 4" by 4". Prepare composites as they will be tested. Preweigh each blotter to be used and record the weight of the blotter.

Set the pipettor to deliver 2 mls of liquid.

Calibrate the automated Blood Strikethrough test unit and set to deliver 1.0 psi pressure for three minutes.

Specific Testing Procedure (for Single Intake/Rewet Test):

Place the rate block (as previously described) with funnel on top of the composite to be tested. Place the tip of the pipettor into the simulant. Fully depress the plunger of the pipettor and release slowly, keeping the tip immersed in the fluid, to partially fill the pipettor. Holding the stopwatch in one hand and the pipettor in the other, depress the plunger of the pipettor to the first stop only to deliver 2 mls of simulant to the funnel of the rate block. Start the timer at the same time the fluid is delivered to the rate block.

Carefully observe the fluid in the center trough of the rate block. Stop the timer as soon as all fluid has penetrated the top layer of the test specimen. Record the time. Leave the rate block in place on top of the specimen for one minute to allow the fluid to move in the absorbent system the entire composite.

Remove the rate block. Place the specimen on the center of the water bottle on the Automated Blood Strikethrough unit and place a pre-weighed blotter on top of the specimen. Record the blotter weight. Start the Strikethrough unit.

After the specimen platform on the Strikethrough unit has returned to the lowered position, remove the specimen and blotter and record the weight of the blotter.

This test is used to determine the amount of fluid that will come back to the surface when a load is applied. The amount of fluid that comes back through the surface is called the "rewet" value. The more fluid that comes to the surface, the larger the "rewet" value. Lower rewet values are associated with a dryer material and, thus, a dryer product. In considering rewet, three properties are important: (1) intake rate, since if the material/system does not have a good intake rate then fluid can rewet, (2) ability of absorbent to hold fluid (the more the absorbent holds on to the fluid, the less is available for rewet), and (3) flowback, the more the cover prohibits fluid from coming back through the liner, the lower the rewet.

Calculations:

Determine the average of time recorded for each different material code.

For each specimen, subtract the dry weight of the blotter from the wet weight to determine the Rewet value. Average the Rewet values for each code.

Triple Intake Rewet/Test Procedure (TIR) or Menses Simulant Intake Rewet Test: Triple Gush:

General Procedure:

The objective of this test is to determine differences between materials and/or materials composites or systems of material composites in the intake rate when 3 sudden fluid insults (gushes) are applied, with time allowed for fluid to distribute in the material(s) between insults. The materials to be tested are prepared in the same way as for the Single Intake Test described above. However, after insulting the first 2 mL load of simulant to the materials, 9 minutes are allowed to pass allowing the fluid to interact with the absorbent system. This step is repeated for a total of 3 insults. Following that, a rewet test as described above is performed and its value is recorded. The insult time is a direct measurement of time for absorption. Smaller values of intake time refer to a more absorbent sample with larger values of intake time refer to a less absorbent sample.

For the purposes of this application the term "masking" shall mean the covering of a stain with a substance or material, such that the stain is not visually perceptible or less visually perceptible than without the substance or material.

As used herein the term "nonwoven fabric or web" means a web having a structure of individual fibers or threads which are interlaid, but not in an identifiable manner as in a knitted fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes. Each of the foregoing patents is hereby incorporated by reference in their entirety.

As used herein, the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers which may be continuous or discontinuous, are generally smaller than 10 microns in average diameter, and are generally tacky when deposited onto a collecting surface. The foregoing patent is hereby incorporated by reference in its entirety.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein, the term "machine direction" or MD means the length of a fabric or a nonwoven material in the direction in which it is produced. The term "cross machine direction" or CD means the width of fabric or a nonwoven material, i.e. a direction generally perpendicular to the MD.

As used herein the term "monocomponent" fiber refers to a fiber formed from one or more extruders using only one extrudate. This is not meant to exclude fibers formed from is one polymer to which small amounts of additives have been added for coloration, anti-static properties, lubrication, hydrophilicity, etc. These additives, e.g. titanium dioxide for coloration, are generally present in an amount less than 5 weight percent and more typically about 2 weight percent.

As used herein the term "conjugate fibers" refers to fibers which have been formed from at least two extrudates extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 4,795,668 to Krueger et al., U.S. Pat. No. 5,540,992 to Marcher et al. and U.S. Pat. No. 5,336,552 to Strack et al. Conjugate fibers are also taught in U.S. Pat. No. 5,382,400 to Pike et al. and may be used to produce crimp in the fibers by using the differential rates of expansion and contraction of the two (or more) polymers. Crimped fibers may also be produced by mechanical means and by the process of German Patent DT 25 13 251 Al. For two component fibers, the polymers may be present in ratios of 75/25, 50/50, 25/75 or any other desired ratios. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes. Each of the foregoing patents are hereby incorporated by reference in their entirety.

As used herein, the term "bonded carded web" refers to webs that are made from staple fibers which are sent through a combing or carding unit, which breaks apart and aligns the staple fibers in the machine direction to form a generally machine direction-oriented fibrous nonwoven web. Such fibers are usually purchased in bales which are placed in a picker which separates the fibers prior to the carding unit. Once the web is formed, it then is bonded by one or more of several known bonding methods. One such bonding method is powder bonding, wherein a powdered adhesive is distributed through the web and then activated, usually by heating the web and adhesive with hot air. Another suitable bonding method is pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using bicomponent staple fibers, is through-air bonding.

As used herein, the term "Airlaying" shall have the same meaning as "airlaid" and is a well known process by which a fibrous nonwoven layer can be formed. In the airlaying process, bundles of small fibers having typical lengths ranging from about 6 to about 19 millimeters (mm) are separated and entrained in an air supply and then deposited onto a forming screen, usually with the assistance of a vacuum supply. The randomly deposited fibers then are bonded to one another using, for example, hot air or a spray adhesive. The absorbent composites of this invention may be made using the airlaid process. The production of airlaid nonwoven composites is well defined in the literature and documented in the art. Examples include the DanWeb process as described in U.S. Pat. No. 4,640,810 Laursen et al. and assigned to Scan Web of North America Inc, the Kroyer process as described in U.S. Pat. No. 4,494,278 Kroyer et al. and U.S. Pat. No. 5,527,171 Soerensen assigned to Niro Separation a/s, the method of U.S. Pat. No. 4,375,448 Appel et al assigned to Kimberly-Clark Corporation, or other similar methods. Each of the foregoing patents are hereby incorporated by reference in their entirety.

As used herein, the term "absorbent article" shall be synonymous with "personal care product" and shall mean diapers, training pants, absorbent underpants, adult incontinence products, veterinary absorbent products, and mortuary products, bandages and feminine care/hygiene products.

As used herein, the term "feminine care products" shall mean absorbent, feminine directed products designed to absorb discharges from the vaginal area, and which are designed to be worn adjacent to the female anatomy as opposed to within the female anatomy. Such products include feminine pads and pantiliners.

As used herein, the term "disposable" includes being disposed of after a single use and not intended to be washed and reused.

As used herein, a "layer" is defined as having a homogeneous composition and density, within typical process variability for nonwoven structures. Alternatively a layer may contain patterns within itself, such as stripes, apertures or waves. "Layer" when used in the singular may have the dual meaning of singular or plural elements.

As used herein, the "upward" or "top" position is closer to the body than "downward", "lower" or "bottom" position when the article is worn.

Words of degree, such as "about", "substantially", and the like are used herein in the sense of, at, or nearly at, when given the manufacturing and material tolerances inherent in the stated circumstances, and are used to prevent the unscrupulous infringer from unfairly taking advantage of the invention disclosure where exact or absolute figures are stated as an aid to understanding the invention.

The term "Insult" refers both to the natural deposition of a body exudate, and in particular urine or menses liquids during personal care product use by a consumer, as well as the deposition of simulated body exudates during personal care product testing.

The phrases "Target", "Target Point", "Target region" or "Target area" are each used synonymously and refer to the area or location on a personal care product where an insult is normally delivered by a wearer, or a nozzle or other device in an experimental method.

As used herein, the term "composite" is defined as having two or more components and may consist of one or more layers. These may be either homogeneous or heterogeneous. It also includes multiple composites which are essentially the same based on structure and surface chemistry.

As used herein the term "multi-layered" laminate shall mean a laminate including two or more layers.

As used herein, the term "absorbent system" is defined as at least two absorbent composites which have complementary structural/surface energy characteristics and are in part in fluid communication with one another.

As used herein, the term "ink jet printing system" is defined to mean the ink jet printer platform (whether it be a drop on demand printer or a continuous printer), and accompanying or associated manufacturing components, such as a continuous feed printing belt on which materials to be printed are passed under an ink jet printer apparatus, and associated power and motor components for moving the materials to be printed through the system.

As used herein and in the claims, the term "comprising" is inclusive or open-ended and does not exclude additional unrecited elements, compositional components, or method steps.

"Pattern bonding" is a method wherein heated calender rolls or ultrasonic bonding equipment are used to bond fibers together, usually in a localized bond pattern, though the web can be bonded across its entire surface if so desired. One example of a pattern is the Hansen Pennings or "HP" pattern with about a 30% bond area with about 200 bonds/square inch as taught in U.S. Pat. No. 3,855,046 to Hansen and Pennings. The HP pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen Pennings or "EHP" bond pattern, which produces a 15% bond area. Numerous other bonding patterns exist. Another suitable and well-known bonding method, particularly when using conjugate staple fibers, is through-air bonding, wherein hot air is passed through the web, at least partially melting a component of the web to create bonds.

As used herein, the term "basis weight" or BW equals the weight of a sample divided by the area measured in either ounces per square yard or grams per square meter. (either osy or gsm)

The term "ink" shall mean any material that can be printed or otherwise desposited on a substrate from via a print process or sprayer system, and in particular materials that can be jetted from an ink jet printer. Inks may be colored or uncolored and may include other additives designed to provide desired attributes to a product. Such additives may include for example biocidal agents, humectants and surfactants.

The term "colored" shall mean containing a colorant or a coloring agent which is visually perceptible to the human eye. For the purposes of this application, such colorant may include pigments or dyes.

The term "uncolored" shall mean not containing a colorant or coloring agent which is visually perceptible to the human eye.

The term "surface" includes any layer, film, woven, nonwoven, laminate, composite, or the like, whether pervious or impervious to air, gas, and/or liquids.

The term "wax" shall mean a low-melting organic mixture or compound that is thermoplastic but solid at room temperature and generally similar in composition to fats and oils. The term can include hydrocarbons, esters of fatty acids, and alcohols. Such materials are typically hydrophobic, but can be engineered wettable, that is made hydrophilic for particular purposes.

The term "liquid impermeable or impervious material" shall mean a material which prevents the passage of liquid at the location to which it is applied, and which can be applied as a liquid, gel, film or fluid or semi-solid but which becomes solid at room temperature, and remains solid when exposed to body temperature or temperatures around body temperature.

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

In accordance with the invention, liquid impermeable materials are applied to various layers of personal care products to enhance the rewet properties of the personal care products, that is, to reduce the demonstrated rewet values of such products. The liquid impermeable materials may in one embodiment be hydrophobic. In an alternative embodiment, the liquid impermeable materials may be hydrophilic.

The present invention relates to any manner of absorbent article/personal care products, such as diapers, training pants, swim pants, incontinence articles, feminine care products, and the like, such as those described for instance U.S. Pat. No. 4,940,464 and WO 037009 which are incorporated by reference hereto in their entirety. The construction and materials used in conventional disposable absorbent personal care products vary widely and are well known to those of skill in the art. A detailed explanation of such materials and construction of conventional personal care products is not necessary for purposes of describing the present invention. However, the invention has particular usefulness for feminine care products, and for purposes of illustration and description only, embodiments of feminine care products according to the invention, in particular feminine care pads/sanitary napkins and/or pantiliners, are referenced herein. It should be appreciated that the invention is in no way limited to such feminine care products in general.

Such liquid impermeable materials are also added to help in masking stains present on such products, which attribute has particular application to feminine care products. Such materials may be deposited on one of more surfaces, of one or more layers, of an absorbent article such as a feminine care product. For instance, such materials may be added onto the liner or surge layers of such products. Furthermore, such materials may be deposited on the top surface of such layers, the bottom surface of such layers, throughout such layers, or any combination of the foregoing. If such liquid impermeable materials are deposited on the lower or bottom surface of liner layers of such products, such materials will not be in contact with a consumer's skin. Likewise, if such materials are deposited on a surge material in such products, it will also not be in direct contact with a consumer's skin.

The liquid impermeable materials (solidified materials) may be translucent and colorless, or alternatively may be translucent and colored (or multicolored). In a further alternative embodiment, such liquid impermeable materials may be opaque and include colorants (one or more) such as dyes and pigments, in order to more effectively mask stains produced in such products while in use. For instance, if the treated layer of a feminine care product is opaque white in appearance, the liquid impermeable material may include titanium dioxide to help mask stains which occur underneath such treated layer. In such a fashion, such colored materials will assist in obscuring stains from layers beneath them, and also blend into the layer over which they are applied. Therefore, in a desired embodiment, the color of the liquid impermeable material is similar to that of the layer on which it is applied. In a further alternative embodiment, the color of the liquid impermeable material is different from the layer color (white for instance) to which it is applied, in order to enhance stain masking of stains from lower layers.

Such liquid impermeable materials are desirably in the form of phase change materials or other materials that are applied as a liquid, gel or paste, and that solidify on the article. Such materials may include adhesives, paints, inks, thermoplastic polymers, and waxes which are applied by spray, extrusion, printing, or various other topical application methods. Desirably, such phase change materials are hot melt wax containing ink jet inks, which are printed via ink jet printers onto one or more personal care product layers, during product manufacture. However, such liquid impermeable materials may additionally be applied to regions of such product layers by other application methods, such as by dip coating. For the purposes of this application, all such application methods shall be referred to herein as "treatments", and such layer materials will be referred to as being "treated" when such treatments have been applied to their surfaces.

Ink jet printing methodology is the desired application method however, as a result of the speed and accuracy of such printing method. Such print methodology allows for the efficient deposit of phase change liquids in the exact locations on a product layer that is desired by a product developer. While the size, shape and prevalence of such treated regions on the various layers may be varied, such as for aesthetic reasons, it is desired in one embodiment that such treated regions be in the forms of similarly sized repeating shapes or areas (solidified deposits of phase change liquid), such as stripes or circular areas, for example. Alternatively, it is desired that such treated regions be in the form of an aesthetically pleasing design, such as a floral pattern. In any event, it is desired in one embodiment that less than or equal to 80% of the treated layer surfaces be covered across their surfaces with the spaced apart solidified deposits. In this embodiment the ratio of treated areas to untreated areas should be at most 4:1. It is desired in another alternative embodiment that less than or equal to 75% of the treated layer surfaces be covered across their surfaces with the spaced apart solidified deposits. The ratio of treated areas to untreated areas should be at most 3:1 in this alternative embodiment. If such regions are in the shapes of stripes, it is desired that each stripe be present having a width amount of between about 0.25 mm and 2.25 mm and desirably be present along the product or layer length, such that the stripes run length wise along the layer's longest dimension (longitudinal direction) across the entire product width (narrowest dimension). In this fashion, such stripes may be deposited on a layer surface or product in the machine direction, as the product or layer travels in-line during the product or layer manufacturing process. Such stripes are desirably in one embodiment of uniform width, from one end of the layer to the other. Alternatively, the width of such stripes or shapes varies along the product length. Such stripes are desirably separated by untreated areas of the layer surface, with said untreated areas of the layer being in widths of between about 0.25 mm and 0.75 mm.

It should be recognized that such stripes can just as easily be situated across the product or layer width, such that the stripes run lengthwise along the layer's narrowest dimension (lateral dimension). In this instance, such stripes could be deposited in the cross-machine direction. No matter what the shape of the treated areas, it is desirable that the treated areas cover between about 25% and 80%, and more desirably between 25% and 75% of the layer's total surface area on the layer that is being treated, and such treatment extends across the entire surface of the treated layer. Furthermore, it is desirable that the applied treatment be applied in an add-on amount of between about 0.3 gsm and 16.0 gsm. While in a desired embodiment, such treatment is in the form of a continuous pattern such as stripes or lines, or alternatively in a discontinuous pattern, such as a series of dots or dashes, it should be appreciated that the aesthetic design may be easily varied to accommodate individual or cultural tastes. For instance, such treatment can be in the form of parallel placed patterns, such as repeating sinusoidal waves or zigzag patterns, or alternatively in the shape of non-abstract design patterns such as repeating roses or other floral designs as illustrated in FIGS. 5A-5D.

In any event, such treatment should allow the passage of body exudates between treated lines, bands, dots, or designs to lower layers of the feminine product or other absorbent article in order to allow absorption of the exudates. Such untreated areas of the liner layer or lower layer, would provide an unimpeded path for body exudates to the absorbent layer within the article. Desirably, such regions are printed on one or more layers of an absorbent article. In an alternative embodiment, such regions may be deposited on at least one surface of a liner layer, and desirably on the top surface of a liner layer, that would be in contact with a user's skin. In another alternative embodiment, such regions may be deposited on the lower surface of a liner layer. In still a further alternative embodiment, such regions may be deposited throughout the thickness of the liner layer, such that the deposits are on both top and lower surfaces.

An example of such a personal care product of the invention is illustrated in FIG. 1, which shows a cross-sectional view of a portion of a feminine care product, namely a feminine care pad. As can be seen in FIG. 1, a feminine care pad 10, is comprised of a multilayered laminate or composite. Such multi-layered laminate includes on its upward facing surface, a printed coating that has been deposited in various regions, 14 of wax-inclusive ink jet ink (phase change liquid). Such ink jet ink is printed onto a generally liquid permeable liner layer 16 in an amount of between about 25% and 80%, desirably between about 25% and 75% surface coverage. Such liner layer is disposed on top of (vertically adjacent) a surge layer or liquid transfer layer 18 which itself is disposed on top of an absorbent layer 20. Each of the various layers is in fluid communication with layers vertically adjacent to them. While not illustrated in the Figure, in use, the feminine care product would also likely include a liquid impermeable outer cover/back sheet layer of hydrophobic materials disposed adjacent the absorbent layer 20 on a side opposite to that of the surge layer. The liner layer and backsheet layer would be sealed together at their peripheral edges utilizing known techniques, such as for example, gluing, crimping, hot sealing or the like, the sealed edges defining an overall sealed periphery edge of the pad. An adhesive layer may also be placed on the exposed surface of the hydrophobic back sheet layer and a further temporary protective release paper may be placed over the adhesive. While the multi-layered laminate illustrates a single treated layer, it should be appreciated that more than one layer can be treated to promote low rewet values and stainmasking functionality for the product. For instance, the surge or other fluid transfer layer may likewise be treated. It should further be appreciated that each of the previously described functional layers may themselves be comprised of one or more layers. Additionally, such product may be constructed without a surge layer.

As is illustrated in the Figure, the deposited coating is located on the top surface of the liner layer. However, in an alternative embodiment, the deposited coating may be applied to the bottom/lower surface of the liner layer (side opposite the currently coated side). In this fashion, the deposited coating would not come in direct contact with the skin of a consumer using the absorbent product.

In one embodiment, application of a hydrophobic treatment to the various layers is topical such that the treatment creates a film-like barrier on a surface of the layer in those areas where it has been applied, and does not prevent the layer from carrying on its normal functions below the topical treatment, i.e. a lower fluid transfer layer continues to move fluid. In an alternative embodiment, the application of hydrophobic treatment penetrates through the thickness of the treated layer such that the stripes, shapes, or designs penetrate the entire thickness of the layer, such as for instance, the liner layer 16. In another alternative embodiment, the deposits are hydrophilic but liquid impervious so as to attract fluid to the deposit surface. Such an embodiment could be utilized in one or more layers, but desirably in the surge layer, so as to reduce rewet sensation on the liner.

The liquid permeable liner layer 16 of the feminine care product has an outwardly facing top surface that may contact the body of the wearer and receive bodily exudate(s). This outwardly facing surface is the surface on which the liquid impermeable material is desirably deposited. The liner layer 16 desirably is made of a material which is flexible and non-irritating to the wearer. As used herein, the term "flexible" is intended to refer to materials which are compliant and capable of readily conforming to the bodily surface(s) with which such materials are in contact, or materials which respond by easily deforming in the presence of external forces.

The liner layer 16 is provided for comfort and conformability and functions to direct bodily exudate(s) away from the body, and toward the absorbent layer 20. The liner layer 16 should retain little or no liquid in its structure so that the cover provides a relatively comfortable and non-irritating surface next to the tissues of the consumer and in the case of a female consumer, within the vestibule of a female wearer. The liner layer 16 can be constructed of any woven or nonwoven material which is easily penetrated by bodily fluids which contact the surface of the layer. Examples of suitable liner layer materials include rayon, bonded carded webs of polyester, spun webs of polypropylene, polyethylene, nylon, or other heat-bondable fibers, polyolefins, such as copolymers of polypropylene and polyethylene, linear low-density polyethylene, and aliphatic esters such as polylactic acid. Finely perforated film webs and net material, and apertured films can also be used as liner layers. A specific example of a suitable liner layer material is a bonded carded web made of polypropylene and polyethylene such as that used as cover stock for KOTEX pantiliners and obtainable from the Sandler Corporation, Germany. Other examples of suitable materials are composite materials of polymer and nonwoven fabric materials. The composite materials are typically in the form of integral sheets generally formed by the extrusion of a polymer onto a web of spunbonded material. The fluid permeable liner layer 16 can also contain a plurality of apertures formed therein which are intended to increase the rate at which bodily fluid(s) can penetrate through the cover/liner and into the absorbent layer 20.

The liner layer 16 (such as in a pantiliner) may also be embossed with any desired embossing pattern to define embossed channels. Embossing techniques are well known to those skilled in the art. An embossing pattern not only creates an aesthetically pleasing surface, the channels also facilitate intake of menses fluid. Menses will tend to flow along the densified edges of the channels rather than pool on contact points of the liner layer 16.

The liner layer 16 can be maintained in secured relation with the absorbent layer 20 by bonding all, or a portion of the adjacent surfaces to one another. A variety of bonding methods known to one of skill in the art can be utilized to achieve any such secured relationship. Examples of such methods include, but are not limited to, the application of adhesives in a variety of patterns between the two adjoining surfaces, entangling at least portions of the adjacent surface of the absorbent layer with portions of the adjacent surface of the liner layer, or fusing at least portions of the adjacent surface of the liner layer to portions of the adjacent surface of the absorbent layer.

The pad 10 includes a surge management layer (surge layer) 18 which helps to absorb, decelerate, and diffuse surges or gushes of liquid that may be rapidly introduced into the pad 10. Desirably, the surge management layer 18 can rapidly accept and temporarily hold the liquid prior to releasing the liquid into the storage or retention portions (absorbent layer) of the pad. The surge layer can be located below the liner layer 16, as illustrated. In an alternate embodiment, a further distribution material layer (not shown) may be disposed between the surge layer 18 and underlying absorbent layer 20 to more evenly distribute the flow of fluids from the surge layer 18 into the absorbent layer 20. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference in their entirety for all purposes.

The feminine care product's absorbency capacity is desirably provided in its absorbent layer(s) with sufficient capacity to absorb and retain the intended amount and type of bodily exudate(s). The absorbent capacity is provided primarily by the liquid retention absorbent layer 20. The absorbent layer 20 can be any structure or combination of components which are generally compressible, conformable, non-irritating to a wearer's skin, and capable of absorbing and retaining liquids and certain body wastes. For example, the absorbent layer 20 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles (also referred to as superabsorbent materials (SAM) or superabsorbent particles (SAP)). The cellulosic fluff may comprise a blend of wood pulp fluff. One desirable type of fluff is identified with the trade designation CR 1654, available from U.S. Alliance of Childersburg, Ala., USA, and is a bleached, highly absorbent wood pulp containing primarily soft wood fibers. Other suitable types of pulp are CF-416 and NB416, available from Weyerhaeuser, U.S.A. The absorbent materials may be formed into a web structure by employing various conventional methods and techniques. For example, the absorbent web may be formed with a dry-forming technique, an air forming (air-laying) technique, a wet-forming technique, a foam-forming technique, or the like, as well as combinations thereof. Methods and apparatus for carrying out such techniques are well known in the art.

As a general rule, the superabsorbent material is present in the absorbent web of the absorbent layer in an amount of from about 0 to about 90 weight percent based on the total weight of the web. The web may have a density within the range of about 0.05 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and desirably is capable of absorbing more than about 25 times its weight in liquid. Suitable superabsorbent materials are readily available from various suppliers. For example, Favor 880 superabsorbent is available from Stockhausen GmbH of Germany; and Drytech 2035 is available from Dow Chemical Company, of Midland Mich., USA.

After being formed or cut into a desired shape, the absorbent web material may be wrapped or encompassed by a suitable wrap that aids in maintaining the integrity and shape of the absorbent structure in the absorbent layer.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

The absorbent web material utilized in the absorbent layer 20 is also selected so that the individual absorbent structure possesses a particular individual total absorbency depending on the intended article of use. For example, for infant care products, the total absorbency can be within the range of about 200-900 grams of 0.9 wt % saline, and can typically be about 500 g of saline. For adult care products, the total absorbency can be within the range of about 400-2000 grams of saline, and can typically be about 1300 g of saline. For feminine care products, the total absorbency can be within the range of about 7-50 grams of menstrual fluid, and can typically be within the range of about 30-40 g of menstrual fluid.

The backsheet layer (not shown) may be any one of a number of suitable liquid impermeable materials known in the art for use as outer covers or baffles in absorbent articles. A specific example of a back cover material is a polyethylene film such as that used in KOTEX pantiliners and obtainable from Pliant Corporation, Schaumburg, Ill., USA. The backsheet layer can be maintained in secured relation with the absorbent layer/liner layer by bonding all or a portion of the adjacent surfaces to one another. A variety of bonding methods known to one of skill in the art can be utilized to achieve any such secured relation. Examples of such methods include, but are not limited to, ultrasonic bonding, thermal bonding, or the application of adhesive materials in a variety of patterns between the two adjoining surfaces.

The liquid impervious material may be a phase change material, such as a hot melt wax inclusive ink. As used herein, the term "phase-change" refers to a material which is processed in a liquid, substantially liquid or semi-solid state and then solidifies or returns to its natural state when cooled. Various phase change liquids may be used with the present invention, for example such liquids may include, but are not limited to, medicaments, inks, waxes, paints, lotions, ointments, skin health agents, topical applications, or combinations thereof. In general, the phase change liquid may be any application or composition which is capable of adhering or being applied to the liner layer 16 or lower layer in the composite, so that, upon solidification, discrete barrier topographies are defined on the liner layer 16 or lower layers. The material or composition is desirably at least partially hydrophobic. The phase change liquid may be, for example, a wax, petrolatum based lotion, adhesive, thermoplastic, and so forth. As used herein, the term "petrolatum" refers to a semi-solid mixture of hydrocarbons obtained from petroleum, such as Glenpure L white petrolatum available from Glen Corporation of St. Paul, Minn. For added benefits, the phase-change liquid may include a skin wellness agent, such as a medicant, emollient, ointment, moisturizer, and the like. Examples of inks for use with the present invention include hot-melt ink jet ink formulations such as those available from Spectra, Inc. of Hanover, N.H., under the brand names SABLE and SABRE, ink formulations available from Tektronix, and those available from Westvaco, and Markem such as 5001 series black inks. Examples of such inks are also described on pages 198-201 of Ink Jet technology and Product Development Strategies, by Stephen F. Pond, copyright 2000, of Torrey Pines Research, which pages are incorporated by reference herein. Additionally, other materials may be used as deposits, such as extruded thermoplastic materials.

Desirably such liquid impermeable material is applied in such a fashion that it does not rupture or alter the surface of the layer to which it is applied. In the case of hot-melt inks, or extruded thermoplastic materials, such inks and materials should have melting temperatures desirably below that of the layer materials to which they are applied.

Figure 4A:
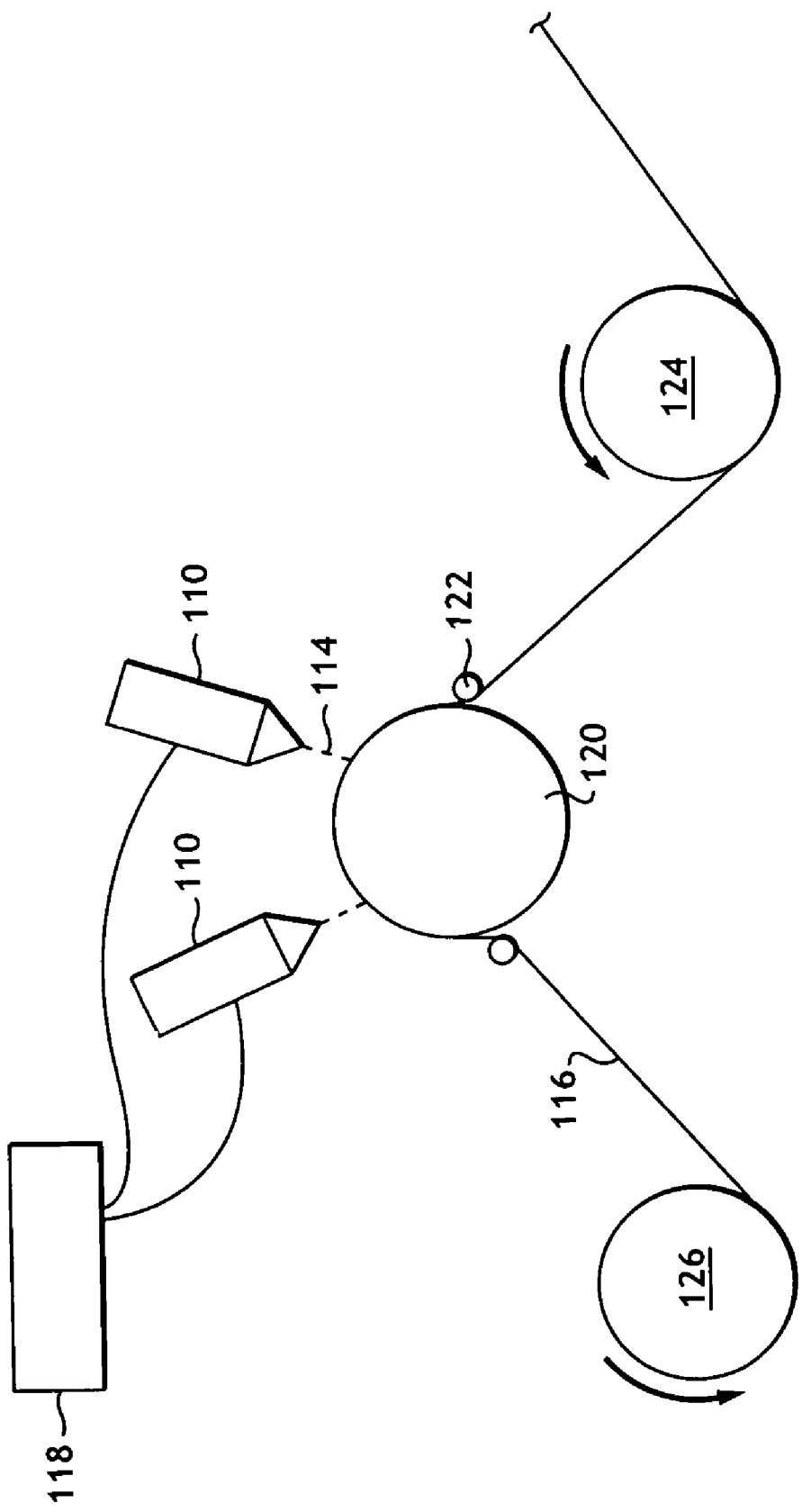
FIG. 4a is a schematic view of a drop on demand (Piezo) ink jet printing system for printing on feminine care products in accordance with the invention.
Figure 4B:
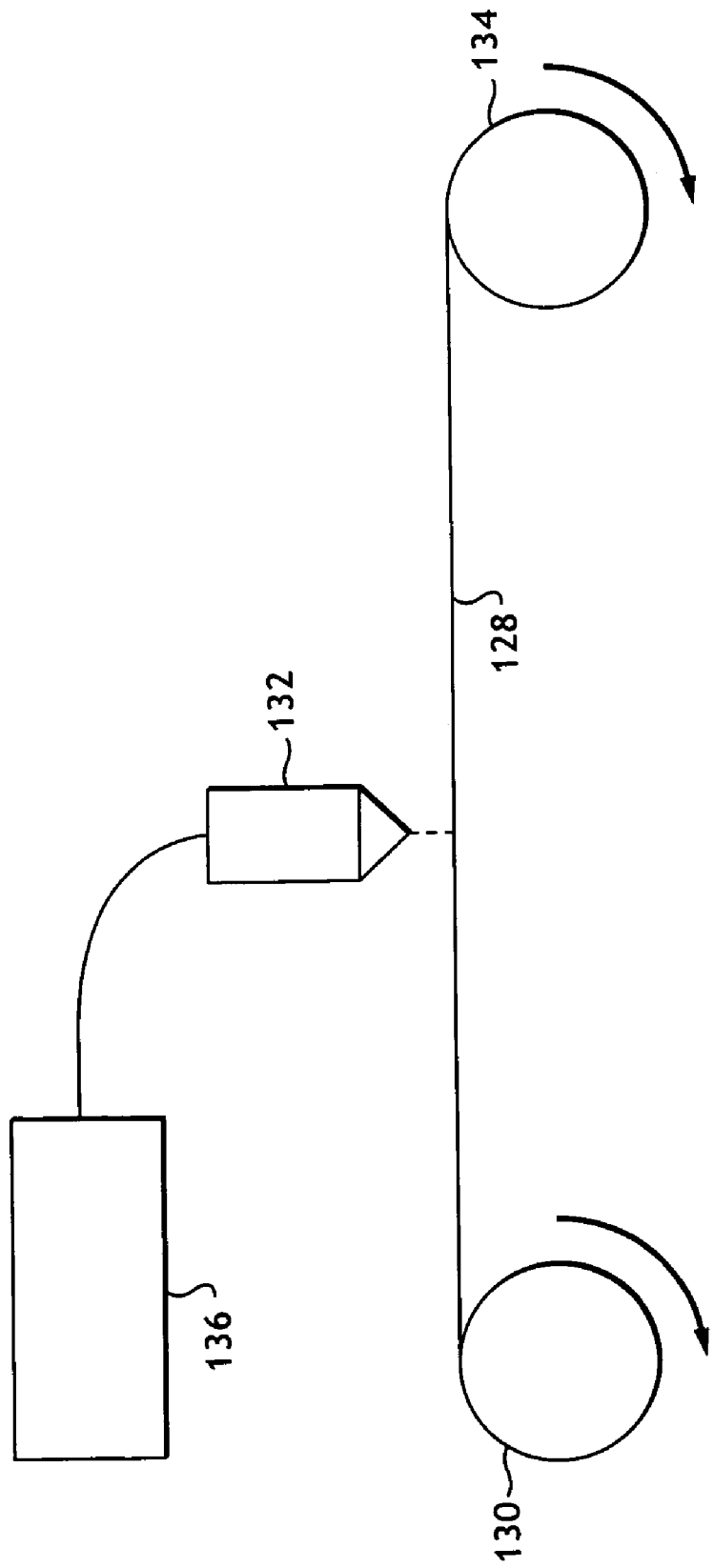
FIG. 4b is a schematic view of a continuous ink jet printing system for printing on feminine care products in accordance with the invention.
Figure 5:
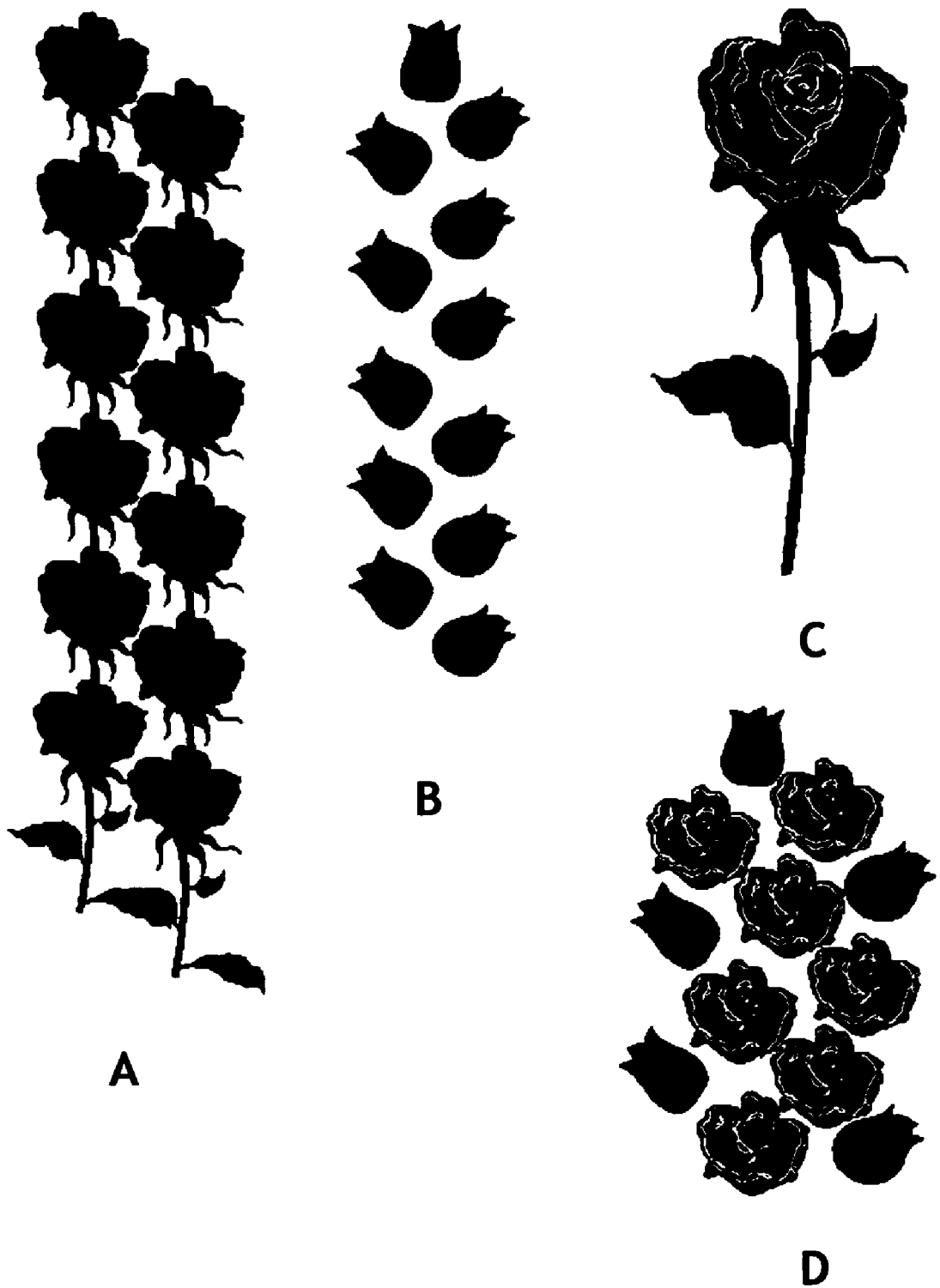
FIGS. 5A-5D is an illustration of an aesthetic pattern for use on products in accordance with the invention.

The liquid impervious material deposits of the phase-change liquid may be applied to the liner layer 16 by various techniques. For example, the phase-change liquid may be deposited by use of a piezo-driven print heads. The piezo-driven print devices are typically capable of emitting droplets having a diameter in the range of about 50-90 micrometers with placement resolution to about $\frac{1}{200}$ of an inch. The phase-change liquid may be deposited in a single or multiple pass of the liner layer 16 or other layer, past the print head, or under the printhead as a single set of streams (if such is a part of the machine direction manufacturing process). In an alternate desirable embodiment, the phase-change liquid is deposited by a continuous inkjet printing technique. For the purposes of illustrating various ink jet application methods, FIGS. 4a and 4b have been provided. FIG. 4a illustrates a method of creating multi-color process images at high speed. The method includes providing at least two high-operating frequency printheads 110 which are capable of processing phase change inks, providing at least two phase change inks 114, providing a substrate 116, activating the printheads such that at least two inks pass therethrough, and passing the substrate 116 under the printheads at a rate of at least about 1000 feet per minute, wherein at least one process image (such as the rose patterns in FIGS. 5A-5D) are formed on the substrate 116. For instance, utilizing this method, stripes or other patterned print can be deposited along the entire surface of the layer or product. Desirably products or layer material, if individual layers are to be printed, move past the printer at about 100 to about 4000 feet per minute. More desirably, products or layer material move past the printer at between about 200 to 1500 feet per minute. Even more desirably, products or layer material move past the printer at between about 400 to 600 feet per minute.

In one embodiment of the method of the present invention the printheads may have operating frequencies of between about 4 kHz-40 kHz, but more desirably between about 15-20 kHz. Any suitable printhead may be used provided it is capable of performing at the frequencies identified with any one or more of the phase change inks discussed herein. As previously indicated, it is desirable for the phase change inks to be hot melt phase change inks, and in some instances more desirable for the phase change inks to be wax based. While reference is made to passing, conveying or otherwise transporting the substrate or material (such as a liner layer, surge layer, or finished feminine care product) under the printhead, the same terminology is also intended to include passing the printhead over the substrate or the combined movement of the printhead and the substrate such that the desired production speeds may be achieved.

The use of phase change inks, and specifically hot melt inks, and more specifically hot melt wax based inks, enables the high speed printing desired herein as the phase change inks do not require any additional significant drying step. Previously, the drying time of inks and compositions used in printers limited production speeds. The use of phase change inks eliminates the need for additional drying steps and/or space between the printheads (for different color applications) which was previously necessary. Thus design registration and image quality may be achieved if desired, without sacrificing high production speeds. In a further embodiment of a print method for manufacturing materials of the invention, a controller or other control means 118 may be provided that is in communication with the printheads. The control means 118 is desirably capable of operating in multiple modes and may control the printheads 110 such that the printheads 110 act together or independently from one another. It will be appreciated that any number of control means are suitable for use with the present invention depending in part on the number of printheads each control means is in communication with. Exemplary control means may vary from manual to computer controlled or computer regulated control elements (e.g. manual switches, line driven switches, photo-optic sensors, and software driven witching circuits).

As illustrated in FIG. 4a, part of the substrate transport system is a drum 120 and a plurality of idlers 122. The drum and idlers 122 are designed to be compatible with the substrate material 116 which is passing over them such that the substrate 116 is in a substantially wrinkle free condition as it passes over or around the drum 120. The idlers 122 may be adjusted such that a desired level of tension may be applied to the substrate material 116 to eliminate or reduce the wrinkles that otherwise might be present in the material 116 were it to pass over the drum 120 without having some tension force applied thereto. That is, the idlers, 122 may be used to create or maintain a desired tension on the material 116 as it passes over the drum 120. It should be appreciated and understood that while a drum 120 is shown in FIG. 4a, the present application is not intended to be limited thereto. Any number of drums or idler combinations may be used. Further, while the spacing between the printheads and the substrate to be printed may vary, it is desirable for the material 116 to be about 2 to 3 mm from the printhead when the ejection of ink occurs. Following printing, the material that has been fed to the drum from feeder roll 124, is then wound about winder roll 126.

In an alternative embodiment of a print method, a substrate 128 to be printed is unwound from a feeder roll 130 and passed under a printhead of a continuous printer 132 that is then rewound on a winder roll 134. As in the previously described ink jet printer system arrangement, a computer controller 136 controls the printhead 132. While the substrate is illustrated as passing between two rolls, it can also travel along a forming wire or continuous belt, depending on manufacturing preferences.

The phase-change liquid is desirably applied at add-on levels of between about 0.3 gsm (grams per square meter) to about 13.0 gsm, desirably less than about 10 gsm, and more desirably between about 2.0 gsm to about 5.0 gsm.

As previously indicated, such phase change liquids (i.e. wax inclusive inks) should be selected such that their application through an ink jet printer is not under conditions that would cause significant damage to the underlying layer (substrate material) to be printed. For instance, the application and application conditions of such inks should be such that they do not rupture either by force or by heating, the layer on which they are being printed. Generally, such hot melt waxes that are applicable for practice of this invention should have melting points between about 70 and 140 degrees C. The actual inks utilized should have a melting point lower than that of the material layer on which they are being printed.

Such wax inclusive inks should be non-allergenic and the contact of such inks to the skin of a user should not cause any noticeable irritations. Further such inks should adhere to the various layers to which they are applied and maintain their integrity and position during use of the product. For added benefits, the liquid impermeable materials may include a skin wellness agent, such as a medicament, emollient, ointment, moisturizer, and the like. For use in personal care product absorbent articles, such as feminine care products, the use of skin-unfriendly components should be avoided.

Figure 2:
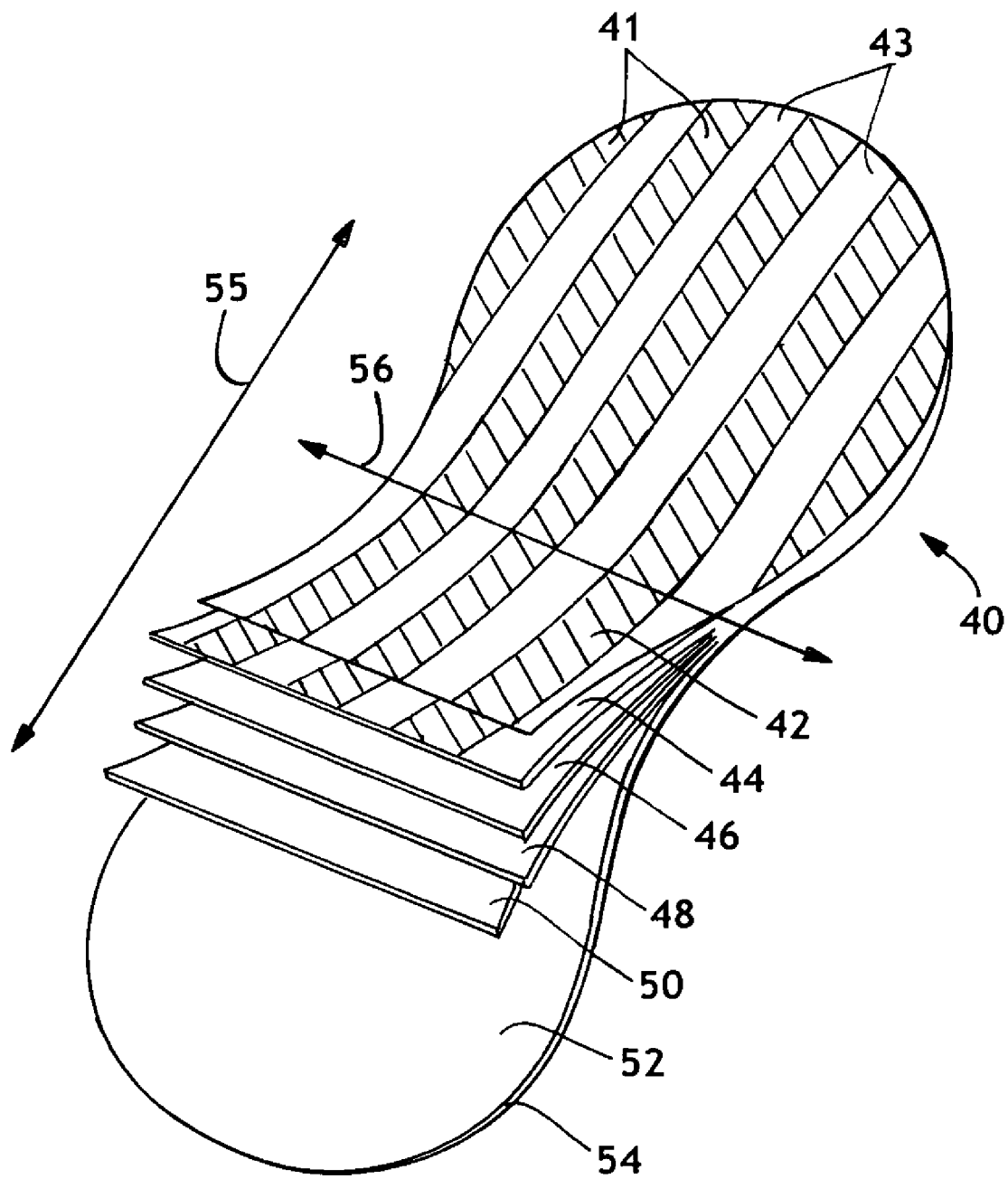
FIG. 2 illustrates an exploded view of an alternative embodiment of a feminine care product (pad) in accordance with the invention.

An alternative embodiment of the invention is illustrated in FIG. 2, which shows an exploded perspective view of a feminine care product in accordance with the invention. The pad will generally have a longitudinal direction 55 ending in longitudinal ends and a lateral direction 56, ending in lateral ends (transverse to the longitudinal ends). Various geometries of such feminine care pads/sanitary napkins are well known to those skilled in the art, and all such embodiments are within the scope and spirit of the invention. As can be seen in the Figure, a feminine pad 40 is comprised of multiple laminate layers. A liner layer 42 has been coated/printed with a series of liquid impervious material (hydrophobic) stripes 41, which are separated by stripes of untreated liner material 43. The stripes have a desirable width of about 1.50 mm (6 jets, where each jet is 0.25 mm wide in the described head). Desirably, the range of such stripes is between about 0.75 mm to 2.25 mm. The stripes are spaced apart a distance of from about 0.25 to about 0.75 mm.

The treatment stripes 41, have been colored with titanium dioxide such that they match the underlying white color of the liner layer. In this fashion such treatment offers some stain masking ability after a liquid has been absorbed into the product, but initially, the stripes look as though they blend into the product layer. The exudates liquid is maintained below the treatment layer (underneath the coating) and is therefore covered by the colored coating. To further hide the stain, a darker color such as blue or black may be utilized.

A fluid transfer layer or surge layer 44 is situated immediately under the liner layer 42. A one or two layer absorbent retention layer 46 and 48, is situated immediately under the fluid transfer layer. The surge layer has also been treated in a stripe pattern similar to that of the liner. While the embodiment illustrates both a liner and surge layer that have been treated, it should be recognized that in alternative embodiments, either of the layers may be treated, without the treatment of the other layer.

A back sheet layer 50 is situated under the lowest liquid retention layer. An adhesive layer (not shown) is situated under the backsheet layer and a release paper 54 is positioned adjacent the adhesive layer such that it can be removed along one side 52 from the adhesive by a simple pulling action. The particulars of each of the various layers in this embodiment may be those previously described for the layers illustrated in FIG. 1.

In still a further alternate embodiment of the current invention, an absorbent article includes a layer with at least one surface that has been treated as previously described, but that also includes at least a two layer absorbent structure/system that can maximize intake, reduce rewet values and also provide increased absorbent capacity. In such an embodiment, the upper layer closest to a liner is a surge material that has been treated in accordance with the current invention on its top surface. The lower absorbent layer is desirably a superabsorbent containing composite. The surge layer of such a structure is desirably a bicomponent through air bonded low density and resilient structure. Such bicomponent fibers may be for example polyethylene/polypropylene side by side bicomponent materials. The lower absorbent layer desirably includes absorbent fibers and superabsorbent materials, such as polyacrylic acid or a polysaccharide.

In the practice of absorbent articles in accordance with the invention, it should be recognized that multiple configurations are possible, and that certain configurations may improve both rewet and stainmasking, but reduce intake performance. For instance, the addition of a surge layer, may reduce the intake times demonstrated, but may add other additional benefits. Furthermore, certain embodiments, may only improve intake and stainmasking. The objectives sought after by a particular product will aid in determining the material combinations most suitable for particular product applications. It should also be recognized that the embodiments described herein are not meant to be limiting.

In practice, such feminine care products may be manufactured such that either during the manufacturing process of each layer, specific layers can be selectively treated with ink jet printers or other application methods, to allow for coating by liquid impermeable materials in various regions, or alternatively, the liner layer of the final product (while attached in the product laminate) may be treated. If separate, the layers of the laminate materials may then be bonded as appropriate such as via thermal point, adhesive or ultrasonic bonding, to form the absorbent article. Following the printing of such a material, either the product may be packaged for distribution, or if the printed material is just an individual layer, the layer may then be incorporated into a final laminate product using known lamination, or bonding methods. Such methods should be utilized so that they either do not re-melt any coating, or puncture the continuous coated regions such that they are rendered ineffective at either reducing rewet or masking stains contained below them.

For the purposes of the trial examples which follow, the following materials were prepared and tested by the described codes. Six sets of trials were conducted with variations in the materials as noted.

The specific materials that were tested are described in the specific example sections that follow. The absorbent layer material used for these studies consisted of a 250 g/m$^2$ airlaid material made of 90% NF401 pulp and 10% Kosa T-255 fiber binder, 0.14 g/cc placed on top of a 175 gsm airlaid material made of 90% NF405 pulp and 10% Kosa plus T-255 fiber binder, 0.08 g/cc, unless otherwise noted. If one of the absorbent layers was used only, it was one of these materials where noted. In some instances, bicomponent spunbond surge materials (between 1.0 and 1.5 osy) was utilized. The surge comprised bicomponent (PP/PE) side by side, thru air bonded spunbond as the second layer where noted. The liner layers typically consisted of 0.6 osy polypropylene spunbond materials. The liners were typically treated with approximately 0.45% Ahcovel. If an ULTRATHIN material was utilized, it consisted of a 0.6 osy spunbond, 250 gsm airlaid, 175 gsm airlaid, and baffle and was obtained from Kimberly-Clark Corporation, of Roswell, Ga. In each of the examples which follow, the ink was applied to one or more layers of materials. Between 1 and 3 passes in an ink jet printer were done for each layer of materials at approximately 50%-100% coverage, using a setting of between about 500-8000 Hertz on a piezo ink jet printer. The ink was blue or black where noted. The inks were Hot Melt Wax Spectra, Inc. inks, and in particular either Clear, Pink, Black or Cyan where noted, such as Jet 7520/Jet 7533, CAS # 1333-86-4 and Jet 5514/Jet 5528. In certain examples, the ink was printed on co-apertured ULTRATHINs available from Kimberly-Clark Corporation. In some examples, a solid film of ink was printed on layers for comparison purposes. In some instances, where noted, a floral Rose Design was printed onto the layer as illustrated in FIGS. 5A-5D. The purpose for using the burgundy colored design of the floral prints was to introduce a color and pattern that would mask the dark red color of menses. As an alternative the printing of the liner layer to mask stains, color could be added to the airlaid layer(s) via the fibers. Additionally, the colored pattern could be printed in such a fashion such that it becomes visible only during use, such as in response to thermal changes.

Otherwise, the ink was printed on in a stripe configuration from one longitudinal end to the other, between about 0.75 mm and 2.25 mm in width (most frequently 1.50 mm width) and 0.75 mm width spacing between stripes, for a liner/surge (as specified) top surface coverage of approximately 50%. It has been found that the treated surface area of liners should be less than or equal to about 75%. The ink images were printed using a Galaxy PH 256/80 HM printer from Spectra.

The actual materials of the first examples are described in a table, followed by testing results in a second table, and likewise for the latter examples. For each of the tests, the materials were prepared by placing individual layers over one another in the order indicated and printing the final feminine care product, as well as the separate printing of individual layers as noted, and then placing them together over each other as noted, for testing.

TABLE 1a

Example 1 Materials

| Code Number | Description of Each layer |
|---|---|
| 1 | UltraThin (As previously described) |
| 2 | One pass solid Printed liner on Ultra Thin |
| 3 | Rose printed liner on Ultra Thin |
| 4 | 3 passes solid printed liner on Ultra Thin |
| 5 | 1 pass solid printed 250 gsm airlaid top and bottom of Ultra Thin |
| 6 | Rose printed on 250 gsm airlaid of Ultra Thin |
| 7 | 3 passes solid printed 250 gsm airlaid of Ultra Thin |
| 8 | 1 pass stripes on 250 gsm airlaid of Ultra Thin |

TABLE 1b

Test Results

| Code | Intake (s) | Rewet (g) |
|---|---|---|
| 1 | 16 | 0.36 |
| 2 | 25 | 0.28 |
| 3 | 18 | 0.37 |
| 4 | 42 | 0.17 |
| 5 | 51 | 0.34 |
| 6 | 22 | 0.07 |
| 7 | >2 min. | NA |
| 8 | 129 | 0.35 |

The first set of examples were tested on ULTRA THIN product. The higher the amount of ink on the product, the higher the intake time. For the first set of examples, code 8 worked well for stain masking and wicking of fluid in the machine direction (length of product). While the cover did not mask the stain as well, the airlaid samples with the solid stripe did mask stains.

TABLE 2a

Example 2 Materials

| Code Number | Number of layers | Description of Each layer | Basis Weight of Each Layer | Purpose of Each Layer |
|---|---|---|---|---|
| 1 | 3 | a. Spunbond<br>b. Airlaid (every other jet on)<br>c. Airlaid | a. 0.6 osy<br>b. 250 gsm<br>c. 175 gsm | a. liner layer<br>b. first absorb.<br>c. sec. absorb |
| 2 | 3 | a. Spunbond<br>b. Airlaid (4 jets on, 6 off)<br>c. Airlaid | a. 0.6 osy<br>b. 250 gsm<br>c. 175 gsm | a. liner layer<br>b. first absorb.<br>c. sec. absorb |
| 3 | 3 | a. Spunbond<br>b. Airlaid (3 jets on, 6 off)<br>c. Airlaid | a. 0.6 osy<br>b. 250 gsm<br>c. 175 gsm | a. liner layer<br>b. first absorb.<br>c. sec. absorb |
| 4 | 3 | a. Spunbond<br>b. Airlaid (2 jets on, 4 off)<br>c. Airlaid | a. 0.6 osy<br>b. 250 gsm<br>c. 175 gsm | a. liner layer<br>b. first absorb.<br>c. sec. absorb |
| 5 | 3 | a. Spunbond<br>b. Airlaid (2 jets on, 6 off)<br>c. Airlaid | a. 0.6 osy<br>b. 250 gsm<br>c. 175 gsm | a. liner layer<br>b. first absorb.<br>c. sec. absorb |
| 6 | 3 | a. Spunbond<br>b. Airlaid (4 jets on, 2 off)<br>c. Airlaid | a. 0.6 osy<br>b. 250 gsm<br>c. 175 gsm | a. liner layer<br>b. first absorb.<br>c. sec. absorb |
| 7 | 3 | a. Spunbond<br>b. Airlaid (gradient)<br>c. Airlaid | a. 0.6 osy<br>b. 250 gsm<br>c. 175 gsm | a. liner layer<br>b. first absorb.<br>c. sec. absorb |
| 8 | 3 | a. Spunbond<br>b. Airlaid<br>c. Airlaid | a. 0.6 osy<br>b. 250 gsm<br>c. 175 gsm | a. liner layer<br>b. first absorb.<br>c. sec. absorb |

TABLE 2b

Test Results

| Code | Intake (s) | Rewet (g) |
|---|---|---|
| 1 | 20 | 0.16 |
| 2 | 27 | 0.07 |
| 3 | 25 | 0.18 |
| 4 | 22 | 0.15 |
| 5 | 20 | 0.30 |
| 6 | 24 | 0.17 |
| 7 | 23 | 0.24 |
| 8 | 24 | 0.18 |

For the second set of examples the intake times were comparable to the control. The rewet values were also similar to the controls. All of the airlaid samples were tested with the previously described liner layers and 175 gsm airlaid on bottom. Code 5 demonstrated the best results with 20 second intake time, but the rewet was 0.30 g, compared with 0.18 g for the control. The control demonstrated a 24 second intake time. The rewet of Code 2 demonstrated a value of 0.07 g. As evidenced from the testing, heavier darker stripes need to be printed onto the layers. The stripes in these examples were approximately 30%-50% surface coverage. The stripes in future testing was approximately 66%-80% surface coverage.

Liner Printing Designed Experiment Data:

The following table contains the results of an experiment to evaluate the following effects. Side of liner printed (body side (top side surface) or product side (lower/bottom side surface)) and printing level on intake and rewet of a feminine care absorbent system. All of the samples were tested were printed at 100% coverage at 8000 hz and 1000 hz respectively. Therefore Heavy printing is approximately 15 gsm add on and Light printing is approximately 1.6 gsm add on.

TABLE 3

The samples were tested using the 2 ml single insult/rewet test with menses simulant.
Marginal Means (Unweighted); variable: REWET
1 (2-level factors), 1 (3-level factors),
30 Runs

| | Rewet Means(g) | Pooled Std.Dev. | Overall Std.Dev. | N | Std.Err. for Mean | −95.00% Conif. Limt | 95.00% Conif. Limt |
|---|---|---|---|---|---|---|---|
| Heavy Printed liner | 0.062 | 0.055 | 0.054 | 10 | 0.014 | 0.034 | 0.090 |
| Light Printed liner | 0.125 | 0.040 | 0.042 | 10 | 0.014 | 0.097 | 0.153 |
| No Printing (control) | 0.149 | 0.030 | 0.033 | 10 | 0.014 | 0.121 | 0.177 |

NOTE: Std.Errs. for means computed from MS Error = .0018317

The material systems tested were all three layer systems consisting of a liner over two absorbent layers. The absorbent layers for all samples tested during the experiment were 250 gsm, 0.14 g/cc Airlaid Upper Layer/175 gsm, 0.08 g/cc Airlaid Lower Layer. The liners were 0.6 osy spunbond with 0.45% Ahcovel treatment. The printing was on the liner. The higher the amount of ink on the product, the lower the rewet values.

TABLE 4a

Example 4 Materials

| Code Number | Description of Each layer |
|---|---|
| 1 | Co-apertured Ultra Thin Pad solid printed liner |
| 2 | Co-apertured Ultra Thin Pad solid printed 250 gsm airlaid |
| 3 | Ultra Thin Pad |

TABLE 4b

Test Results

| Code | Intake (s) | Rewet (g) |
|---|---|---|
| 1 | 111 | 0 |
| 2 | 35 | 0.21 |
| 3 | 26 | 0.15 |

For the previous example, for code 1, the intake time was high, but the rewet value was zero g. Code 2 showed very good intake time and good rewet. This performance is comparable to Code 3 which is the control ULTRATHIN product. However, stain masking was considerably better for Code 2 as the stain was barely visible.

For each of the following various examples, the spunbond comprised polypropylene spunbond. The surge comprised bicomponent (PP/PE) side by side, thru air bonded spunbond as the second layer where noted. For each of the codes, the material was printed with an ink jet printer.

TABLE 5

Example 5
Materials and Test Data

| Code | Intake (s) | Rewet (g) |
|---|---|---|
| 1 spunbond liner 250 and 175 gsm airlaid absorbent. | 54 | 0.23 |
| 2 colored spunbond liner colored surge colored 250 gsm airlaid absorbent | 11 | 0.26 |
| 3 spunbond liner surge colored 250 gsm airlaid absorbent | 11 | 0.11 |
| 4 colored surge colored 250 gsm airlaid absorbent | 7 | 0.31 |
| 5 apertured ULTRATHINs | 23 | 0.33 |
| 6 apertured ULTRATHINs with colored liner | 23 | 0.29 |
| 7 surge over airlaid (no ink) | 60 | 0.33 |
| 8 ULTRATHIN with no transfer delay layer and colored surge | 10 | 0.15 |
| 9 ULTRATHIN with colored liner and colored surge | 11 | 0.17 |
| 10 apertured ULTRATHIN | 24 | 0.31 |
| 11 apertured ULTRATHIN and colored 250 gsm airlaid | 34 | 0.21 |

The 175 gsm airlaid was not ink jet printed. The 1.5 osy colored surge is bicomponent spunbond as previously described. The term colored means that the material was inkjet printed with blue wax ink.

Wax ink was treated on a liner as described and joined with a 1.5 osy, 3.8 denier surge material. All of the surge tested had intake times of 13 seconds or below using the Single Intake Test Method described above. Of particular performance, was code 8 having printed surge and demonstrating 10 sec. intake, 0.15 g rewet and good stain masking.

Example of Articles Containing a Layer With Superabsorbent:

Incorporation of superabsorbent (SAP) is desired in an alternative embodiment of a product to provide an efficient means to absorb and retain fluid. One of the drawbacks of SAP is that it tends to hinder the intake rates of fluid. It has been found that absorbent systems containing ink-jet treated surge upper layers combined with SAP, containing lower layers can provide fast intake functionality, low rewet functionality, and high retention capacity in a thin profile. Absorbents of this arrangement were prepared and evaluated for performance.

TABLE 6

Test Results
Printed Surge Data:
The following codes were tested using the Triple gush/rewet test methods. Three 2 ml insults of menses simulant with 9 minutes between insult. All of the codes consisted of three layers of material. A liner (0.6 osy spunbond, 0.45% Ahcovel treatment) and two absorbent layers. The absorbent layers are specified in the code Column.
Triple intake results for surge and SAM testing

| Code | 1st Intake Avg. (s) | 1st Intake S.D. | 2nd Intake Avg (s) | 2nd Intake S.D. | 3rd Intake Avg (s) | 3rd Intake S.D. |
|---|---|---|---|---|---|---|
| 250 gsm 0.14 g/cc | 47.9 | 7.7 | 191.2 | 56.4 | did not go in after 9 minutes | |

TABLE 6-continued

Test Results
Printed Surge Data:
The following codes were tested using the Triple gush/rewet test methods. Three 2 ml insults of menses simulant with 9 minutes between insult. All of the codes consisted of three layers of material. A liner (0.6 osy spunbond, 0.45% Ahcovel treatment) and two absorbent layers. The absorbent layers are specified in the code Column.
Triple intake results for surge and SAM testing

| | | | | | | |
|---|---|---|---|---|---|---|
| Airlaid UL/175 gsm 0.08 g/cc Airlaid LL 1.0 osy surge UL/ 300 gsm 0.14 g/cc, 85% Fluff and 15% Favor 880 SAP LL (300 gsm) | 16.6 | 6.6 | 35.5 | 8.0 | 74.4 | 21.4 |
| Light Printed Surge UL/ 300 gsm 0.14 g/cc, 85% Fluff and 15% Favor 880 SAP LL (300 gsm) | 25.8 | 5.2 | 78.7 | 25.3 | 130.2 | 33.8 |

| Code | Rewet Avg (g) | Rewet S.D. |
|---|---|---|
| 250 gsm, 175 gsm | not done | NA |
| surge, SAM | 0.50 | 0.18 |
| Light Printed Surge, SAM | 0.25 | 0.12 |

For the purposes of abbreviation, "UL" shall mean upper layer and "LL" shall mean lower layer. "SD" shall mean standard deviation, and SAM shall mean superabsorbent materials. The light printed surge was printed at 100% surface coverage at 1000 hz, 28 fpm for a gsm add on of approximately 1.9 gsm. The rewet was significantly reduced by light printing on the surge. As can been seen from the table, the combination of ink-treated surge with 15% SAP/85% Fluff containing lower layer, provides relatively fast intake, with a relatively low rewet (approximately half of a surge/SAM structure without ink printing), as well as the added capacity from superabsorbent materials.

Printed ADD-ON Levels:

100% coverage at 8000 Hertz, 28 fpm deposited approximately 15.6 gsm of ink to the sheet based on basis weight differences between printed and non-printed paper control. The paper control had total ink capture by sheet. Therefore, the actual ink jet add-ons were slightly less than the calculated values due to incomplete capture of the ink by the base sheet being printed.

The following table contains the calculated maximum add-on levels for various materials made and tested during the ink jet printing trials.

TABLE 7

| Printing Conditions | Gsm add on |
|---|---|
| 100% at 8000 hz, 28 fpm | 15.60 |
| 80% at 8000 hz, 28 fpm | 12.48 |

TABLE 7-continued

| Printing Conditions | Gsm add on |
|---|---|
| 75% at 8000 hz, 28 fpm | 11.70 |
| 66% at 8000 hz, 28 fpm | 10.30 |
| 50% at 8000 hz, 28 fpm | 7.80 |
| 25% at 8000 hz, 28 fpm | 3.90 |
| 100% at 1000 hz, 28 fpm | 1.95 |
| 80% at 1000 hz, 28 fpm | 1.56 |
| 75% at 1000 hz, 28 fpm | 1.46 |
| 66% at 1000 hz, 28 fpm | 1.29 |
| 50% at 1000 hz, 28 fpm | 0.98 |
| 25% at 1000 hz, 28 fpm | 0.49 |

TEST/EXAMPLE CONCLUSIONS

In order to help mask staining within the absorbent layer of a feminine care product, ink was added to many different feminine care materials. When the material was is run through a series of bench tests, it was determined that the rewet property of the materials was significantly improved (rewet reduced), that is the amount of moisture that returned to the surface of a feminine care product was reduced. The specific inks that were used employed waxes. The samples were run through the rewet test under 1 psi. In each of the testing, the distance of the print head from the sample was approximately between one and three mm.

It should be appreciated by those skilled in the art that various modifications and variations can be made to the embodiments of the absorbent article described herein without departing from the scope and spirit of the invention as set forth in the appended claims and equivalents thereof.

We claim:

1. An absorbent article, comprising:
a liquid permeable liner layer having a top surface and a lower surface, said top surface defining a liner top surface area;
a generally liquid impermeable outer cover;
an absorbent layer disposed between said liner layer lower surface and said outer cover;
a series of spaced apart solidified deposits of a liquid impermeable material defined on said liner layer lower surface and spaced across said lower surface wherein less than or equal to 80% of said liner surface area is covered with said spaced apart solidified deposits, the deposits being adhered to said liner layer lower surface to maintain position during use of the article, wherein the liquid impermeable material does not contact a user's skin during use of the article, and wherein the spaced apart solidified deposits define a design.

2. The absorbent article as in claim 1, wherein less than or equal to 75% of said liner surface area is covered with the spaced apart solidified deposits.

3. The absorbent article as in claim 2 wherein said article comprises either a feminine care product, a diaper, a training pant, or an adult incontinence product.

4. The absorbent article as in claim 2, wherein said article is a sanitary napkin, pad, or pantiliner.

5. The absorbent article as in claim 2, wherein said deposits comprise spaced apart continuous stripes disposed on said top surface.

6. The absorbent article as in claim 5 wherein said stripes have a width of about 1.50 mm.

7. The absorbent article as in claim 5 wherein said stripes are spaced apart a distance of from about 0.25 to about 0.75 mm.

8. The absorbent article as in claim 2, wherein said deposits comprise spaced apart discontinuous patterns disposed on said top surface.

9. The absorbent article as in claim 2, wherein said deposits comprise phase change liquid.

10. The absorbent article as in claim 9, wherein said phase change liquid is one of an ink, wax, petrolatum based lotion, adhesive, thermoplastic, or combination thereof.

11. The absorbent article as in claim 10 wherein said phase change liquid comprises a skin wellness additive.

12. The absorbent article of claim 2 further including at least one additional layer disposed between said liner layer and said absorbent layer, said additional layer having a top surface and a lower surface.

13. The absorbent article of claim 12 wherein said additional layer includes across either its top, lower, or both top and lower surfaces, a series of spaced apart solidified deposits of a liquid impermeable material.

14. The absorbent article of claim 2, wherein the absorbent layer contains superabsorbent material in the concentration of between about 10-30% by weight.

15. A feminine care product, comprising:
a liquid permeable liner layer having a top surface and a lower surface;
a generally liquid impermeable outer cover layer;
an absorbent layer disposed between said liner layer lower surface and said outer cover layer;
spaced apart solidified deposits of a phase-change liquid defined on said liner layer lower surface across the lower surface of said liner layer, the deposits being adhered to said liner layer lower surface to maintain position during use of the product, wherein the phase-change liquid does not contact a user's skin during use of the article, and wherein the spaced apart solidified deposits define a design.

16. The feminine care product as in claim 15, wherein said phase-change liquid is one of an ink, wax, petrolatum based lotion, adhesive, and thermoplastic.

17. The feminine care product as in claim 15, wherein said deposits comprise a series of spaced apart continuous deposits of said phase-change liquid.

18. The feminine care product as in claim 15, wherein said spaced apart continuous deposits comprise generally parallel stripes.

19. The feminine care product as in claim 18, wherein said stripes have a width of about 1.50 mm and are spaced apart a distance of from about 0.25 to about 0.75 mm.

20. The feminine care product as in claim 15, wherein within said top surface a ratio of exposed surface area of said liner to treated surface area of said liner is at most about 3:1.

21. The feminine care product of claim 15 further including at least one additional layer disposed between said liner layer and said absorbent layer, said additional layer having a top surface and a lower surface.

22. The absorbent article of claim 21 wherein said additional layer includes across its top surface a series of spaced apart solidified deposits of a liquid impermeable material.

23. The feminine care product of claim 15, wherein the absorbent layer contains superabsorbent material in the concentration between about 10-30% by weight.

24. A feminine care product including an upper layer having a top and lower surface, with said lower surface being treated with ink across said lower surface such that no more than 80 percent of said lower surface is covered with ink, and said feminine care product also including a lower layer containing superabsorbent, wherein the ink does not contact a user's skin during use of the article, and wherein the ink defines a design.

* * * * *